(12) United States Patent
Kashanin et al.

(10) Patent No.: US 11,633,737 B2
(45) Date of Patent: Apr. 25, 2023

(54) MICROFLUIDIC CHIP FOR FOCUSSING A STREAM OF PARTICULATE CONTAINING FLUID

(71) Applicant: Cellix Limited, Dublin (IE)

(72) Inventors: Dmitry Kashanin, Dublin (IE); Igor Shvets, Dublin (IE); Francesco Dicorato, Dublin (IE)

(73) Assignee: Cellix Limited, Dublin (IE)

( * ) Notice: Subject to any disclaimer, the term of this patent is extended or adjusted under 35 U.S.C. 154(b) by 392 days.

(21) Appl. No.: 16/095,107

(22) PCT Filed: Apr. 20, 2017

(86) PCT No.: PCT/EP2017/059453
§ 371 (c)(1),
(2) Date: Oct. 19, 2018

(87) PCT Pub. No.: WO2017/182599
PCT Pub. Date: Oct. 26, 2017

(65) Prior Publication Data
US 2019/0232290 A1 Aug. 1, 2019

(30) Foreign Application Priority Data
Apr. 20, 2016 (EP) .................................. 16166177

(51) Int. Cl.
| | | |
|---|---|---|
| *G01N 15/10* | (2006.01) | |
| *B01L 3/00* | (2006.01) | |
| *C12M 1/00* | (2006.01) | |
| *G01N 15/14* | (2006.01) | |
| *G01N 15/00* | (2006.01) | |

(52) U.S. Cl.
CPC ... *B01L 3/502776* (2013.01); *B01L 3/502746* (2013.01); *B01L 3/502761* (2013.01);
(Continued)

(58) Field of Classification Search
None
See application file for complete search history.

(56) References Cited

U.S. PATENT DOCUMENTS 5,972,710 A * 10/1999 Weigl .................... B01F 5/0403
422/81
6,437,551 B1 * 8/2002 Krulevitch ......... G01N 33/5438
324/649

(Continued)

OTHER PUBLICATIONS

Claudio Cupelli et al., "Leukocyte enrichment based on a modified pinched flow fractionation approach," Microfluidics and Nanofluidics, 14:3-4, pp. 551-563, Published online Nov. 8, 2012 (14 pages).

(Continued)

*Primary Examiner* — Paul S Hyun
(74) *Attorney, Agent, or Firm* — Bookoff McAndrews, PLLC

(57) ABSTRACT

A microfluidic chip for focussing a stream of particulate containing fluid comprises a sample microfluidic channel configured to receive the stream of particulate containing fluid, a guidance microfluidic channel having a polygonal cross-sectional area and configured to receive a stream of guidance fluid, and a common microfluidic channel having a polygonal cross sectional area formed by the merging of the sample microfluidic channel and the guidance 10 microfluidic channel at an oblique angle along only part of one or more sides of the guidance microfluidic channel, and a detection zone disposed in the common microfluidic channel having one or more sensors. The merging of the sample microfluidic channel and the guidance microfluidic channel is configured to provide a composite fluid stream containing a focussed beam of particulates that is disposed asymmetrically in the common microfluidic channel 15 adjacent a corner or side of the common microfluidic channel and wherein the one or more sensors are configured for sensing (Continued)

a characteristic of the focussed beam of particulates in the common channel.

16 Claims, 26 Drawing Sheets

(52) U.S. Cl.
CPC ......... *C12M 47/04* (2013.01); *G01N 15/1404* (2013.01); *G01N 15/1459* (2013.01); *G01N 15/1484* (2013.01); *B01L 2200/0636* (2013.01); *B01L 2200/0652* (2013.01); *B01L 2300/0645* (2013.01); *B01L 2300/0663* (2013.01); *B01L 2300/0861* (2013.01); *B01L 2400/0463* (2013.01); *B01L 2400/0469* (2013.01); *G01N 2015/0038* (2013.01); *G01N 2015/0053* (2013.01); *G01N 2015/1006* (2013.01); *G01N 2015/1402* (2013.01); *G01N 2015/1413* (2013.01)

(56) References Cited

U.S. PATENT DOCUMENTS

| | | | |
|---|---|---|---|
| 2003/0102854 A1* | 6/2003 | Gascoyne | G01N 15/1218 324/71.4 |
| 2005/0068536 A1* | 3/2005 | Schwabe | G01N 21/6428 356/436 |
| 2008/0093306 A1 | 4/2008 | Oakey et al. | |
| 2012/0063664 A1 | 3/2012 | Di Carlo et al. | |
| 2012/0084022 A1* | 4/2012 | Giovangrandi | G01F 1/584 702/45 |

OTHER PUBLICATIONS

Hamed Amini et al., "Fluid-Particle and Fluid-Structure Interactions in Inertial Microfluidics," Electronic Thesis and Dissertations, University of California, Dec. 31, 2012, available online at http://escholarship.org/uc/item/4kh876bb.pdf (124 pages).

Tao Sun et al. "Single-cell microfluidic impedance cytometry: a review" Microfluidics and Nanofluidics, 8:4, pp. 423-443, Published online Mar. 6, 2010 (22 pages).

Unyoung Kim et al., "Simultaneous sorting of multiple bacterial targets using integrated Dielectrophoretic-Magnetic Activated Cell Sorter," Lab on a Chip, 9:16, Published online May 14, 2009 (6 pages).

International Search Report and Written Opinion in International Application No. PCT/EP2017/059453 dated Jun. 21, 2017 (16 pages).

* cited by examiner

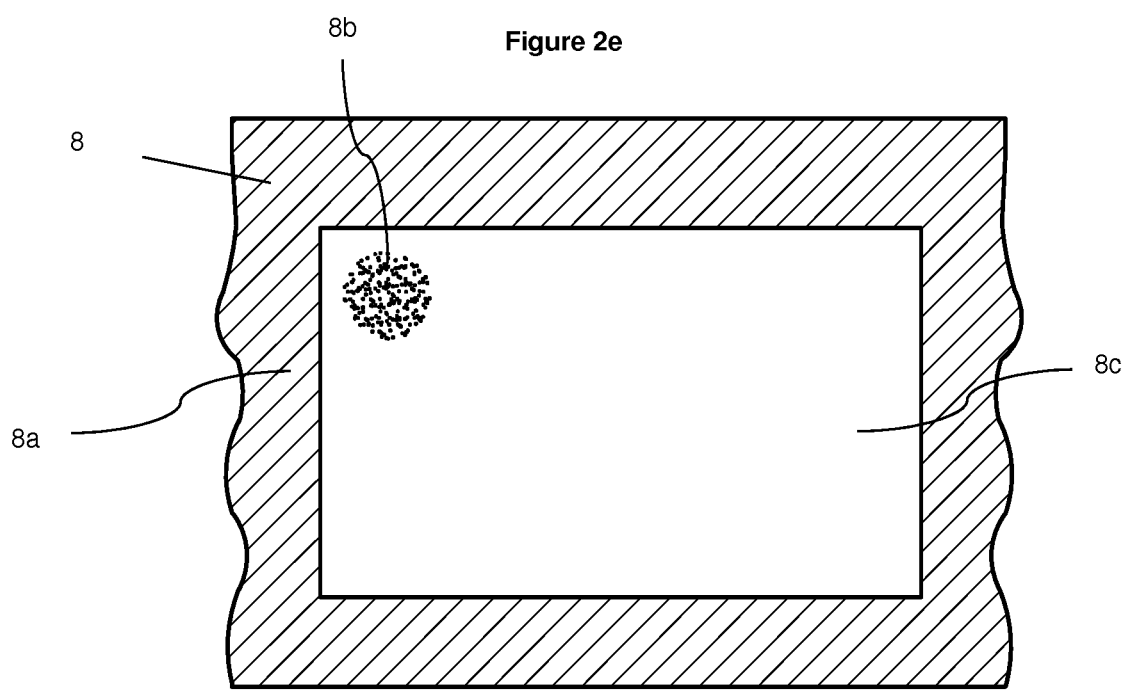
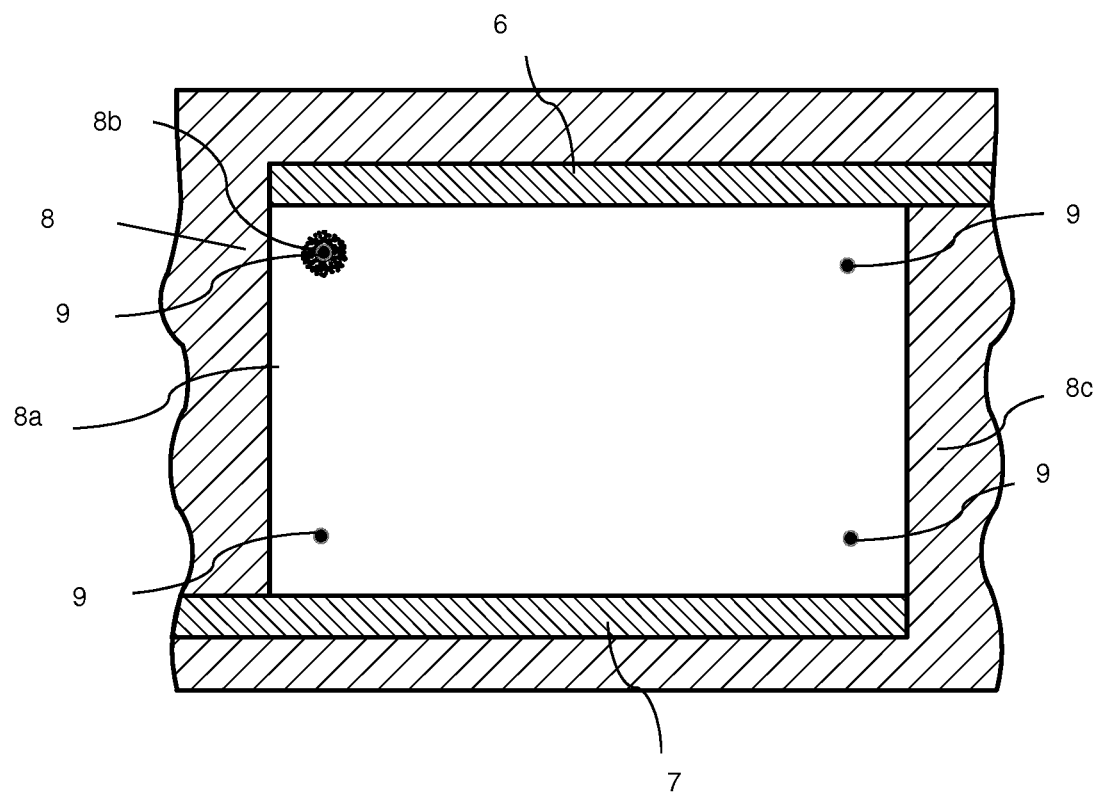

ial stage under 35 U.S.C.
MICROFLUIDIC CHIP FOR FOCUSSING A STREAM OF PARTICULATE CONTAINING FLUID

CROSS-REFERENCE TO RELATED APPLICATION(S)

This application is the U.S. national stage under 35 U.S.C. § 371 of International Application No. PCT/EP2017/059453, filed on Apr. 20, 2017, which claims priority to European Application No. 16166177.2, filed on Apr. 20, 2016, the entireties of each of which are incorporated by reference herein.

TECHNICAL FIELD

The invention relates to a microfluidic chip and method for focussing a stream of particulate containing fluid and optionally analysing the focussed stream of particulate containing fluid. In one aspect, the microfluidic chip is for impedance spectroscopy or optical scattering based analysis, identification or separation of particulate containing fluids. In another aspect, the microfluidic chip is for impedance spectroscopy or optical scattering or fluorescence based analysis, identification or separation of cell containing fluids, especially fluids containing different sub-populations of cells.

BACKGROUND TO THE INVENTION

Note, for the purpose of this invention the term "particles" or "particulates" will be used to describe solid particles, e.g. particles of metals, oxides, nitrides, sulphides, polymer particles and particles of numerous other inorganic and organics materials, also mixed particles containing blends and composites of materials within individual particles and various nano- and micro-particles and clusters, semi-solid particles such as jells. The term will also be used to describe soft particles e.g. polystyrene beads and acrylic beads or indeed blends of soft particles and their compositions, blends and compositions involving soft matter materials and solid matter materials in each particle. The term will also be used to describe cells, e.g. mammalian cells and/or any other cells. For the purpose of this invention, the particle is a contained object whose properties differ from those of the liquid carrying it.

Convention flow cytometry relies on alignment of cells within the sample liquid in a train and detecting, identifying the cells in one-by-one fashion. For example, the cells could be aligned in a train that passes through an optical detection beam, so that cells come into the focused beam of the detection apparatus one cell at a time and the identification is based on optical signal altered by the cell, e.g. scattering of light or fluorescence signal. The same approach is applied in the case of counting and identification of particles in a particle containing fluid. In this disclosure we will consider both, the fluid containing cells and fluid containing particles, and for brevity shall call them both particulate containing fluid. The focus of attention of this invention is the methods and apparatus for such detection and identification that performs the measurements in a microfluidic format.

Currently in conventional flow cytometry, a stream of particles or cells is positioned within a detection zone that sometimes is also called "flow cell", by applying a stream of sheath fluid, which surrounds the stream of particulate containing fluid and coaxially focuses the sample stream to achieve uniform flow of cell passing the detector one-by-one. Typically, the flow rate of the sheath stream is one-to-two orders of magnitude greater than of the sample stream to achieve appropriate focusing ratio and obtain the sample stream of 30-70 micrometers in diameter that is a suitable size for the optical-detection-based cytometers. In the fluorescence scattering flow cytometry, flowing cells or particles pass through a focused laser beam inside the detection channel and scattering of laser light is measured. Two directions of light scattering are detected independently: forward light scattering, which contains information about the particles size and side light scattering, which contains information about internal properties of the cell or particles. Additionally, side light scattering signal might be subject to light filtering in order to extract information about certain fluorescence emission bands of the particle or cell.

It is important to note that hydrodynamic focusing is necessary to reduce variation of scattered light signal by making sure that all particles or cells are subjected to the same intensity of laser light and pass through the focused laser beam uniformly. Uniformity implies uniformity of the trace of the cells or particles in the focused laser beam as this affects the intensity of the detected signal. If the particles or cells are not of circular shape as they often are, uniformity also refers to of their orientation with respect to the focused beam direction. Indeed if the cells are e.g. discoid, then the optical signal will change depending on whether they face the optical beam facing with larger area side (flat face) or smaller area side (edge of the discoid).

Particles or cells then can be divided into subpopulations based on their respective fluorescence intensities in a certain fluorescence band. These subpopulations could correspond to respective staining of particular cell receptors, cytoplasm or nucleus. It is becoming more important to differentiate particles or cells, which differ by minute change of particular cell properties. For example, accurate measurement of cell size allows detecting abnormal red blood cells amongst healthy red blood cells. Ability to differentiate cell shape allows detection of sickle cells and for differentiation of different types of bacteria, for example rod shaped E-coli or circular shaped Staphylococci bacteria. Measurement of content of the cell nucleus allows for example for differentiation of X and Y bearing chromosomes in spermatozoa cells. Such measurements of minute difference of these cell properties are beyond current advancements in conventional flow cytometry. The main limitation preventing more accurate measurements is inability of current techniques to present all the cells or particles in the particulate fluid in front of the detector in a reproducible and accurate manner.

In recent years, there is increasing interest in implementing cell flow cytometry devices in a microfluidic format. Microfluidics provides a convenient technology platform to miniaturize conventional scattering flow cytometry making construction and manufacturing of conventional flow cytometry detection channel simple, miniature while also making the whole device disposable.

There are several examples of microfluidic flow cytometers utilizing fluorescence and impedance detection on chip in order to count the cells and to evaluate cell properties. In article "Microflow cytometer with integrated hydrodynamic focusing", Marcin Frankowski et. al. [6] describes several configurations of integrated cytometer on microfluidic chip including hydrodynamic focusing and also describes experiments with fluorescence detection of calibration beads with various fluorescent intensities. The method provided allows for low CV of measurements for intensity of particles around 3%, which is comparable with conventional flow cytometry measurements. Moreover, authors have experimented with detection of fluorescently tagged lymphocyte subpopulation, with results comparable with those of conventional cytometry.

The publication "Microfluidic impedance cytometer for platelet analysis", Mikael Evander et.al [10] describes impedance—based flow cytometer including two dimensional hydrodynamic focusing with dielectric sheath for the detection of platelets among red blood cells. To calibrate the system, authors used 10 μm and 5 μm polystyrene beads and measured the impedance signal produced by the beads at various ratios of sample and sheath fluids. As a result, they have achieved best signal and lowest variation by using dielectric sheath and at the core sample stream width of 33 μm, versus initially used 145 μm. The authors have also experimented with TRAP activated platelets versus non-activated platelets from healthy donors and were able to detect the differences between the two populations.

The inventors have also investigated impedance flow spectroscopy method of cell detection where two pairs of electrodes are used similar to configuration described in [10], each pair having an excitation and measurement electrodes. An AC voltage at radio frequency from 100 KHz-100 MHz is applied to an excitation electrodes and an electrical current is measured by the measurement electrodes. The electrical current being measured is then amplified and converted into an output voltage. The output signal is then demodulated to remove excitation frequency and to recover impedance magnitude and phase. As a cell passes through the pair of excitation and measurement electrodes, impedance magnitude and phase change, thus recording the information about the cell properties. Additional pair of electrodes ensures measurement is differential thus eliminating parasitic electromagnetic noise.

Typically, the measurement is taken at low frequency: 200 KHZ-500 KHZ to acquire information about the cell size and at high frequency 2-50 MHz to acquire information about the cytoplasm and internal properties of the cell.

FIG. 1a displays density plot of impedance magnitude versus phase for a population of identical polystyrene beads. The beads are polystyrene beads of 6 μm in diameter. In this experiment the channel is of a square cross-section (30 μm×30 μm) and there are two electrodes deposited on the channel with the size of 20 μm×0.2 μm: the top electrode deposited on the upper wall of the channel (ceiling of the channel) is the excitation electrode and the electrode at the lower wall of the channel (floor of the channel) is the detection electrode. When particles pass in between the excitation and the detection electrode, they induce a significant variation in complex value of impedance comprised of variations in the magnitude of the impedance and also the variation in the phase of the impedance, equivalent to variation in real and imaginary parts of impedance. FIG. 1a plots this data for a fluid containing the polystyrene beads in the format of magnitude vs phase that is convenient for further discussion. We have experimentally confirmed that at low frequency the impedance signal depends on the cell size and also on the cell position within the microfluidic channel. Moreover, we proved that signal is different for the cells flowing at the top of the channel and close to excitation electrode versus those flowing at the bottom of the channel and close to measurement electrode. The difference is partly due to non-uniformity of the electric field between two electrodes of a finite width. Additionally, there are differences of electric field gradient at the top and at the bottom of the channel; especially, the electric field gradient is greater at the excitation electrode compared to the one at the measurement electrode. This also contributes to the sensitivity of impedance signal to the cell position at high frequencies. Similarly, FIG. 1b displays the scatter of the data points from a population of red blood cells in the same format of impedance magnitude versus impedance phase. We shall refer to this format of data presentation as impedance density plot. It is important to note that in both cases of polystyrene beads and red blood cells measurements, we have not employed any hydrodynamic focusing or positioning of the sample, and yet achieved separation of homogeneous population into several distinct subpopulations. Further we give explanation of this phenomenon and will provide the method to utilize it to our advantage.

It is known from the prior art publications that there are situations when distribution of particles flowing across the rectangular microchannel is inherently non-uniform. Moreover, depending on particle velocity and size, the particles arrange into preferred stable positions, which are typically not in the center of the rectangular microchannel. These hydrodynamically favored positions might be influenced by ratio of width and the height of the channel (square channels versus rectangular channels), and also by the velocity and the size of the particles, viscosity of fluid and by the Reynolds number and the densities of the particles and the liquid moving the particles. The self-focusing of particles is often referred to as an inertial particle focusing which occurs at the flows with Reynolds number higher than unity (Stokes flow) and lower than one hundred. This ordering occurs due to four lateral forces acting on the particle flowing in the rectangular walled channel: Magnus force due to slip-rotation, Saffman force due to slip-shear, wall lift force due to the disturbance of flow field around particles from wall, and shear gradient lift force due to the parabolic curvature of the undisturbed velocity profile [2].

In publication "Fundamentals and Applications of Inertial Microfluidics: A Review" Jung Zhang et. al. [1] provides a review of advances in inertial focusing and summarizes situations where stable positions are influenced by geometry of the channels. According to the article, if flown in a circular channel, randomly distributed particles migrate towards stable positions, which are located equidistantly and 0.6 times of the channel radius from the circular channel axis. In a square straight channel, where width is equal to depth of the channel, particles focus normally in four equilibrium positions facing the center of each wall. If the channels are rectangular and the aspect ratio is less than 0.5 (the width is at least 2 times higher than the depth) there are only two stable positions at the centers of longer walls. This phenomenon is explained by Jian Zhou et. al. [3] and it is due to a two-stage inertial focusing. Moreover, techniques described in Dino Di Carlo et. al. [4] allows for the focusing of particles in the stable positions and simultaneously for the rotation of non-circular particles, where rotational alignment is observed with the disk of discoid particles parallel to the wall of the channel.

Additional to the inertial focusing, there are number of hydrodynamic sample focusing techniques implemented on a chip where microfluidic channels are added to the detection channel in order to position sample stream within the detection channel. These additional channels carry sheath fluid, which is similarly to conventional flow cytometry, envelops the sample carrier fluid. There are number of 2D focusing techniques focusing in a single plane. More recently, 3D focusing techniques emerged with additional focusing perpendicular to the plane. These are described and referenced below.

Hydrodynamic focusing is known for decades. The phenomenon was described as early as in the year 1883 [O.

Reynolds, Proc. R. Soc. London, 1883, 35 84-99] and it was originally related to the confinement of the sample flow flanked on both sides by sheath flow streams. The cross-section of the sample liquid flow in a flow cytometer is typically in the range of 0.003-0.03 mm$^2$.

Hydrodynamic focusing is particularly important for the detection of cells and particles on a chip utilizing impedance measurements. Indeed, for identification of cells (or particles) it is necessary to arrange these in such a flow that they pass in front of the detection system one by one. This "one cell-by-one cell" principle is fundamental for the successful cell identification: one needs to avoid the situation of multiple cells passing through the detection system at once as it could prevent the identification. Making the channel so small that cells (particles) align there one by one due to the tight cross-section of the channel, is not practical: such a small channel that is comparable in cross-section with a single cell, is prone to blockage and it would also require a significant pressure difference as the friction of the laminar flow against the walls increases with decreasing channel cross-section. Therefore, it is common to use hydrodynamic focusing. Hydrodynamic focusing is based on injection of the sample fluid into the laminar flow of sheath fluid. The two flows then merge into to a single channel, usually of a reduced cross-section. This reduces the cross-sections of both, the sheath fluid part of the flow and also the sample liquid flow, and thus achieves the desired reduction in the cross-section of the sample fluid flow. To control the cross-section of the sample fluid, one could change the flow rates of the sample fluid and sheath fluid. For example, the flow rate of the sheath fluid could be increased to reduce the cross-section of the sample fluid. Such a small cross-section of the sample fluid flanked by the flow of the sheath fluid passes through a channel of a rather large cross-section, i.e. multiple of the cell size, that does not block. One could say that microfluidic focusing replaces the hard walls of microfluidic channel for fluid quasi-walls and this reduces the risk of the microchannel blocking. In relation to the electrical impedance based cytometry, hydrodynamic focussing reduces the width of the conductive sample stream to the appropriate size of the cells, increasing the percentage resistance change in the conductive path when a cell passes by.

In recent years, microfluidic impedance cytometry has been further developed to count and discriminate between different kinds of cells. Multi-frequency impedance measurements can be used to determine the electrical properties of single cells in a microchip [S. Gawad, L. Schild, P. H. Renaud, Micromachined impedance spectroscopy flow cytometer for cell analysis and particle sizing, Lab. Chip. 2001 1 76-82;

T. Sun and H. Morgan, Single-cell microfluidic impedance cytometry: a review, Microfluid. Nanofluid, 2010, 8, 423-443]. In these methods cells flow between miniature electrodes which have an AC field applied across them. As the cell passes between the electrodes, the current path is disturbed and the change in current gives a change in the impedance signal associated with a single cell. Usually, impedance measurements at the frequency of (1-5 MHz) give information on the cell membrane capacitance whilst much higher frequencies (>10 MHz) probe the internal properties of the cell. Two or more frequencies can be applied simultaneously to differentiate different types of cells. Impedance flow cytometry can readily detect a cell, and the original technique was developed by Coulter for this. When it comes to more challenging task of separating the sub-populations of cells within the sample fluid, the performance of the impedance cytometry is much less convincing due to large spread in the data points corresponding to each cell. Integration of 3D hydrodynamic focusing with a conventional type microfluidic chip is also not simple. The performance of such on-chip 3D focusing has limited capability.

To reduce the CV of the impedance cytometry it is desirable to be able to direct the sample flow through a well-defined point in between the electrodes, e.g. the center of the channel. This reduces the spread in the data points from a single population of cells of type of particles in the flow. It may also be desirable to align all the cells (particles) in the same way with respect to the direction of the electric field created by the electrodes. Cells often do not have an overall spherical shape but are rather elongated, ellipsoidal or discoid in shape. The signal from the cell in electrical impedance cytometry device depends on the orientation of the elongated axis of the cell with respect to the electrodes.

In recent years, there is increasing body of work on the use of hydrodynamic focusing in microfluidic chips and microchannels. For example, the Japanese patent laid-open No 2003-107099 discloses a "fractionation microchip having a channel for introducing a particulate-containing solution, and a sheath flow forming channel arranged on at least one lateral side of the of the introducing channel. The fractionation microchip further has "a particulate measuring section for measuring the particulates introduced, at least two particulate fractionating channels disposed on the downstream side of the particulate measuring section so as to perform fractional collection of the particulates, and at least two electrodes disposed in the vicinity of channel ports opening . . . so as to control the moving direction of the particulates." The particulate fractionation microchip disclosed in Patent 2003-107099, is so designed that fluid laminar flows are formed by a "trifurcated channel" having a channel for introducing a particulate-containing solution and two sheath flow-forming channels. In essence this is a 2D hydrodynamic focussing on a chip. In the particulate fractionation microchip disclosed in Patent 2003-107099, the trifurcated channel ensures that the particulate-containing solution is sandwiched by the flows of the sheath liquid from the left and right sides, and the particulates are made to flow through the center of the channel in the particulate measuring section. As a result, in the case of measuring the particulates optically, for example, each of the particulates can be accurately irradiated with measuring light. Similar approach is described in [R. Rodriguez-Trujillo, C. Mills, J. Samitier, G. Gomila, Microfluid. Nanofluid, 3 171 (2007)] and [P. Walsh, E. Walsh, M. Davies, Int. J. Heat Fluid Flow 28 44 (2007)].

The 2D hydrodynamic focussing has its intrinsic limitations. With this in mind, there is an increased effort to introduce a 3D hydrodynamic focussing on a microfluidic chip to confine the sample in both, the horizontal and vertical directions. One solution for integration of such 3D focussing with a conventional type microfluidic chip is described in ["Three-dimensional hydrodynamic focussing in a microfluidic Coulter counter", R. Scott, P. Sethu, C. K. Harnett, Rev. Sci. Instruments 79 046104 (2008)]. The focussing is achieved in using a two-level design, the sheath fluid enters the microfluidic chip from a channel that is both, wider and taller than the sample stream.

A similar approach is described in ["Universally applicable three-dimensional hydrodynamic microfluidic flow focussing" Yu-Jui Chiu, S. H. Cho, Z. Mei, V. Lien, T. F. Wu, Y. H. Lo, Lab Chip 2013 13 1803] [Ref 7]. That study deals with three-dimensional hydrodynamic focusing where the sample channel and the two sheath channels having a greater height than the sample channel, join at the junction before the main channel which has the same height as the sheath channel. The merging of channels of different heights produces flow confinement both in the lateral and transverse directions, resulting in 3D focused flow. In that publication, 3D focussing refers to the confinement of sample flow to a straight line at the centre of a channel of a conventional microfluidic planar chip. The authors of that publication state that "particles have a tendency to settle in positions away from the centre of the channel. The flow focussing needs to counter such effects". Therefore, the trend in the microfluidic devices is to position particles at the centre of the microfluidic channel.

In the patent WO 2008/125081 A1 Theisen Janko et al provides the method for focusing fluid in microfluidic channel structure and the implementation of such a microfluidic structure to achieve hydrodynamic focusing of fluid. In this patent, the sample-carrying channel is located in the center and the two sheath flow channels join the sample channel from the sides. To achieve 3 dimensional focusing the first sheath flow channel joins in the bottom layer and from the right-hand side and the second sheath flow channel joins in the top layer and from the left hand side. This configuration creates a swirling motion of fluids and confined the sample stream in between the sheath fluid streams. Although the patent provides a way to focus particles within the channel, the swirling motion does not allow controlling orientation of discoid or non-circular shaped particles.

In the patent US 2009/0283148 A1, Shinoda et. al. [8] teaches of the method of three dimensional hydrodynamic focusing where the microtube is inserted into the microchip to providing the sample flow. The microchip is constructed in such a way that the sheath fluid streams surround the microtube and therefore sheath fluid coaxially focuses particle containing sample stream. This is very similar to the conventional flow cytometry focusing nozzle with only difference that the method is provided to encapsulate the microtube into the microchip structure versus bulky flow cytometry three-dimensional hydrodynamic focusing nozzle.

In the article "A robust electrical microcytometer with 3-dimensional hydrofocusing", Nicholas Watkins et. al. [9] describes the method of focusing where the particle focused in two stages. First the particles are focused in the lateral direction by two sheath streams from the left and the right-hand side. This then followed by so-called "chimney" structure, which forces particles towards the bottom of the channel and where the electrodes are located.

Another approach to three dimensional focusing described in "Two simple and rugged designs for creating microfluidic sheath flow", Peter B. Howell Jr. et. al. This method utilizes a simple planar microfluidic chip in which two channels sheath carrying channel and sample carrying channel join into the main channel. Directly after the intersection the sheath and the sample stream flow side by side and the sample stream is being squeezed to one side of the main channel. Inside the main channel series of groves are placed, which guide sheath fluid stream and wraps it around sample stream. Furthermore, the article provides configuration in which two sheath streams are used, which are joined from either side of sample stream and then the main channel have series of chevron groves to wrap sheath around the sample stream. In "A hard microflow cytometer using groove-generated sheath flow for multiplexed bead and cell assays", Abel L. Twangawng et.al. used similar configuration of chevrons to confine sample stream. They have obtained circular sample stream using only three chevrons, while by using 7 chevrons they were able to achieve an elongated narrow elliptical stream of sample. This precision focusing was further used for detection and differentiation of multiple types of bacteria, which was not possible by conventional cytometer from Luminex. "Multi-wavelength microflow cytometer using groove-generated sheath flow", Joel P. Golden et.al. used similar chevron idea and combined it with fiber optic illumination and detection on a microfluidic chip in order to detect sub-micrometer sized particles.

The hydrodynamic focusing methods described above mainly use symmetrical focusing, similar to coaxial focusing in conventional flow cytometry and position the cells in the center of the main channel. Furthermore, the methods do not take into account hydrodynamically stable positions of flowing particles and the fact that center is the unstable place to position the particles into. This is typically result in the loss of precise focusing within several hundreds of micrometers from the place where sheath fluid meets the sample stream and initial focusing occurs. Although it is adequate for the conventional cytometry, but it does not allow for differential measurement where sample is interrogated several times while flowing through detection channel. Additionally, despite an ability to focus particles in stable positions, inertial focusing is extremely dependent on velocity, viscosity and hydrodynamic properties of particles and does not provide universal method of positioning of particles and cells.

From the review of current state of the art it is evident that prior art solutions do not completely solve the problem of variation of signal due to the particle positioning and orientation within microfluidic channels. It is an object of the invention to overcome at least one of the above-referenced problems.

STATEMENTS OF INVENTION

The invention describes a microfluidic chip and method that provides on-chip hydrodynamic focussing of a particulate containing fluid stream enabling improved on-chip analysis of the focussed stream be means of optical or electrical sensors. The microfluidic chip of the invention is configured to provide a focussed beam of particulates at an asymmetric focal point in the cross section of a microfluidic channel, which focal point has been found to be hydrodynamically favoured (it is more stable that a symmetrical focal point) and that also reduces variation in signal during analysis of the focussed stream. Asymmetric focussing of the particulates in the stream is achieved by merging a particulate containing stream in a sample microfluidic channel with a guidance stream in a guidance microfluidic channel to form a common microfluidic channel containing a composite fluid stream containing a focussed beam of particulates that is disposed asymmetrically with regard to the cross-section of the common microfluidic channel. The asymmetric position is generally disposed towards a corner or side of the cross-section of the common channel. One methods of achieving this is by merging of the sample microfluidic channel and the guidance microfluidic channel at an oblique angle along only part of one or more sides of the guidance microfluidic channel, for example along only a part of one side, or only part of two adjacent sides, of the guidance channel. This geometry forces the particulates in the common channel into a focussed beam at a hydrodynamically favoured focal point in the cross-section of the common channel, where the focussed beam is stable and resistant to de-focussing, such that the particulates pass the detection zone in the focussed beam where the statistical spread of data measured from the particulates is reduced. Examples of suitable microfluidic chip architecture are provided in FIGS. 2 to 19. The use of the microfluidic chip of the invention to sort bovine sperm cells according to sex employing impedance spectroscopy is described with reference to FIGS. 21 to 25.

In a first aspect, the invention provides a microfluidic chip for focussing a stream of particulate containing fluid. The chip typically comprises a sample microfluidic channel configured to receive the stream of particulate containing fluid and a guidance microfluidic channel configured to receive a stream of guidance fluid. The chip typically comprises a common microfluidic channel formed by the merging of the sample microfluidic channel and the guidance microfluidic channel, generally at an oblique angle. The merging of the sample microfluidic channel and the guidance microfluidic channel is generally configured to provide a composite fluid stream containing a focussed beam of particulates that is typically disposed asymmetrically in the common microfluidic channel.

In one embodiment, the merging of the sample microfluidic channel and the guidance microfluidic channel is configured to provide a composite fluid stream containing a focussed beam of particulates that is disposed adjacent a corner or a side of the common channel.

In one embodiment, the chip is configured such that the sample microfluidic channel and the guidance microfluidic channel are merged at an oblique angle along only part of one or more sides of the guidance microfluidic channel, for example along only a part of one side, or only part of two adjacent sides, of the guidance channel.

In one embodiment, the sample microfluidic channel has a polygonal cross-section, for example rectangular (including square), triangular. In one embodiment, the polygon has 3-6 sides, preferably 3-4 sides.

In one embodiment, the sample microfluidic channel has a rectangular cross-section.

In one embodiment, the guidance microfluidic channel merges with the sample microfluidic channel along three or less sides of the polygonal or rectangular sample microfluidic channel.

In none embodiment, the guidance microfluidic channel merges with the sample microfluidic channel along two sides of the polygonal rectangular sample microfluidic channel.

In one embodiment, the guidance microfluidic channel merges with the sample microfluidic channel along one side of the sample microfluidic channel.

In one embodiment, the sample microfluidic channel has a substantially square cross-section.

In one embodiment, the sample microfluidic channel has a non-polygonal cross-section for example a circular or oval, or other non-polygonal cross-section. In such cases, the guidance microfluidic channel merges with the sample microfluidic channel such that the focussed beam of particulates in the common channel is disposed away from a geometric centre of the common microfluidic channel, for example disposed towards a side of the common channel.

In one embodiment, the guidance microfluidic channel has a polygonal cross-section.

In one embodiment, the guidance microfluidic channel has a rectangular cross-section.

In one embodiment, the guidance microfluidic channel has a substantially square cross-section.

In one embodiment, the cross-sectional area of the guidance microfluidic channel is greater than the cross-sectional area of the sample microfluidic channel.

In one embodiment, the cross-sectional area of the guidance microfluidic channel is at least 1.5 times greater than the cross-sectional area of the sample microfluidic channel.

In one embodiment, the cross-sectional area of the guidance microfluidic channel is at least 2 times greater than the cross-sectional area of the sample microfluidic channel.

In one embodiment, the cross-sectional area of the guidance microfluidic channel is at least 3 times greater than the cross-sectional area of the sample microfluidic channel.

In one embodiment, the guidance microfluidic channel and the sample microfluidic channel have different aspect ratios. This is illustrated in FIGS. 2, 4, 6, 8, 10, 12, 14, 16, 18, 19 and 20.

In one embodiment, the at least part of the sample microfluidic channel proximal to a merging zone and the common microfluidic channel are co-extensive along a common longitudinal axis, wherein the guidance microfluidic channel has a longitudinal axis that is oblique to the common longitudinal axis.

In one embodiment, the guidance microfluidic channel and sample microfluidic channel merge over a distance of 100 µm to 5 mm, 100 µm to 4 mm, 100 µm to 3 mm, 500 µm to 5 mm, 500 µm to 4 mm, 500 µm to 3 mm, or 1-5 mm, 1-4 mm, or 1-3 mm.

In one embodiment, the microfluidic chip of the invention is configured for analysis of a focussed stream of particulate containing fluid, for example qualitative or quantitative analysis of the particulate containing fluid. Thus, the chip can analyse whether the particulates comprises a homogenous or heterogenous population, or can separate the particulates into separate populations.

In one embodiment, the microfluidic chip includes a detection zone comprising one or more sensors configured for sensing a characteristic of the focussed stream of particulates in the common channel.

In one embodiment, the sensors are configured for sensing an optical and/or electrical characteristic of the focussed stream of particulates in the common channel. In one embodiment, the at least one sensor is an optical sensor. In one embodiment, the at least one sensor is an electrical impedance-based sensor. In one embodiment, the at least one sensor is configured to detect a characteristic of the focussed stream of particulates in the common channel, typically identify or differentiate particulates, suitably by means of impedance spectroscopy, fluorescence detection or optical scattering.

In one embodiment, the one or more sensors include one or at least two optical waveguides, typically including a waveguide coupled to a light source and a waveguide coupled to an optical detector configured to detect changes in an optical signal corresponding to the focussed stream of particulates passing between the waveguides.

In one embodiment, the one or more sensors include at least one pair of electrodes configured to detect impedance changes. In one embodiment, the at least one pair of electrodes include an excitation electrode and a detection electrode configured to detect AC impedance changes in the common channel corresponding to the focussed stream of particulates passing between the electrodes.

In one embodiment, the one or more sensors are disposed at least 100 µm distally from a point in which the sample and guidance microfluidic channels are fully merged. In one embodiment, the one or more sensors are disposed at least 200 µm distally from a point in which the sample and guidance microfluidic channels are fully merged. In one embodiment, the one or more sensors are disposed at least 300 μm distally from a point in which the sample and guidance microfluidic channels are fully merged. In one embodiment, the one or more sensors are disposed at least 400 μm distally from a point in which the sample and guidance microfluidic channels are fully merged. In one embodiment, the one or more sensors are disposed at least 500 μm distally from a point in which the sample and guidance microfluidic channels are fully merged.

In one embodiment, the one or more sensors are disposed less than 5000 μm distally from a point in which the sample and guidance microfluidic channels are fully merged. In one embodiment, the one or more sensors are disposed less than 4000 μm distally from a point in which the sample and guidance microfluidic channels are fully merged. In one embodiment, the one or more sensors are disposed less than 3000 μm distally from a point in which the sample and guidance microfluidic channels are fully merged. In one embodiment, the one or more sensors are disposed less than 2000 μm distally from a point in which the sample and guidance microfluidic channels are fully merged.

In one embodiment, the microfluidic chip is configured to separate the particulates into two or more sub-populations of particulates, for example 3, 4 or 5 sub-populations. In one embodiment, the microfluidic chip comprises a separation zone (generally distal of the detection zone) comprising a force generator configured to exert a force on the focussed beam of particulates in the common channel to displace an individual particulate in the stream in response to changes in in the optical or electrical characteristics of the focussed stream of particulates corresponding to the individual particulate detected by the at least one sensor.

In one embodiment, the common microfluidic channel branches into two or more channels in the separation zone. In one embodiment, the force generator is disposed to displace one or more particulates from one channel into a different channel.

In one embodiment, the composite fluid stream containing a focussed beam of particulates focussed stream of particulate fluid has laminar flow. In one embodiment, the composite fluid stream has a Reynold Number of 1-1000. In one embodiment, the composite fluid stream has a Reynold Number of 10-500. In one embodiment, the composite fluid stream has a Reynold Number of 50-200. Methods of calculating the Reynolds number for a stream of fluid in channels of various geometries are described in [14].

In one embodiment, the particulates are cells. Other types of particulates that can be analysed using the apparatus and methods of the invention are described below. In one embodiment, the apparatus is for sorting a heterogenous population of particulates into two or more homogenous populations. In one embodiment, the apparatus is for sorting cells according to phenotypic differences. In one embodiment, the phenotypic difference is selected from: cell type; cell sex; disease status; and cell health. In one embodiment, the apparatus and methods of the invention relate to sorting of different populations of cells (for example, sorting epithelial cells from bone marrow cells). In one embodiment, the apparatus and methods of the invention relate to sorting of different sub-populations of cells (for example, sorting different sub-populations of epithelial cells). In one embodiment, the apparatus and methods of the invention relate to sorting of sperm cells according to sex (for example, sorting bovine sperm cells into X and Y populations of sperm cells). In one embodiment, the apparatus and methods of the invention relate to sorting of a population of cells into living cells and dead cells. In one embodiment, the apparatus and methods of the invention relate to sorting of a cell population into cancerous cells and non-cancerous cells. In one embodiment, the apparatus and methods of the invention relate to sorting of a population of cells into healthy cells and unhealthy cells.

In one embodiment, the merging of the guidance and sample channels in the microfluidic chip is configured to provide a focussed beam of cells (or particulate) in the common channel in which the particulates are in single file. In one embodiment, the merging of the guidance and sample channels in the microfluidic chip is configured to provide a focussed beam of cells (or particulate) in the common channel in which the particulates are aligned in the same direction. In one embodiment, the merging of the guidance and sample channels is configured such that non-uniformly shaped particles are aligned along a plane of detection (i.e. between the electrode or optical waveguide sensors).

In one embodiment, the at least one sensor is configured to sense at a focal point in the cross-section of the common channel that corresponds to the position of the focussed beam of particulates.

In one embodiment, the hydrodynamic focussing apparatus is configured to provide anisotropic alignment of the particulates in the composite stream so that the particulates are preferentially aligned with respect to the sensor such that the difference in optical or impedance responses of different particles in amplified.

In one embodiment, the detection zone comprises a plurality of sensors, for example 2, 4, 6, 8, 10, 12, 14, 16 or 18 sensors. In one embodiment, the plurality of sensors include at least one optical sensor and at least one electrical-based sensor (i.e. impedance sensor).

In one embodiment, the detection zone comprises a plurality of sensors in the same detection plane (i.e. disposed around the common channel at the same point along the channel).

In one embodiment, the detection zone comprises a plurality of sensors in different detection planes (i.e. disposed at different points along the channel).

In one embodiment, the sensor comprises an excitation sensor (excitation electrode or waveguide) disposed in one detection plane and a detection sensor (detecting electrode or waveguide) disposed in a second detection plane.

In one embodiment, the microfluidic chip comprises two or more layers, wherein the microfluidic channel is substantially orthogonal to the layers (i.e. it extends through the two or more layers). In one embodiment, the detection zone spans more than one layer. In one embodiment, the detection zone spans 2, 3, 4, 5 or 6 layers. In one embodiment, at least two of the layers comprise an electrode pair. In one embodiment, an excitation electrode of an electrode pair is disposed in one layer and a detection electrode of the same electrode pair is disposed in a second layer.

In one embodiment, the invention provides an apparatus comprising a microfluidic chip according to the invention. In one embodiment, the apparatus comprises an electrical supply module. In one embodiment, the electrical supply module is configured to energise the excitation electrode of the at least one pair of electrodes with AC voltage in the frequency range of 100 KHz to 100 MHz. In one embodiment, the apparatus comprises a sample fluid supply module. In one embodiment, the apparatus comprises a particulate containing fluid supply module. In one embodiment, the fluid supply modules are configured to provide the fluid in laminar flow. In one embodiment, the fluid supply modules are configured to provide a guidance fluid having a flow rate greater than the flow rate of the sample fluid.

In one embodiment, the apparatus is configured such that the AC impedance change detected by the at least one pair of electrodes comprises amplitude and phase characteristics of the AC voltage induced at the detection electrode.

In one embodiment, the channels of the microfluidic chip are configured to provide a composite stream of fluid in which one or both of the core stream and the guidance stream has an elongated cross section.

In one embodiment, the elongated stream is elongated in the plane of the at least one sensor.

In one embodiment, the elongated stream is elongated in a plane perpendicular to a plane of the at least one sensor.

In one embodiment, the channels of the microfluidic chip are configured to provide a composite steam of fluid in which a longitudinal axis of the particulate (core) stream is offset with respect to a longitudinal axis of the guidance stream.

In one embodiment, the cross-sectional area of the common microfluidic channel in the detection zone is in the range of 0.0001-0.09 mm². Cross sectional area of 0.0001 to 0.001 are considered to be small and correspond to channels of 10-30 μmin width and depth. Cross sectional area of 0.001 to 0.01 are considered to be medium and correspond to channels of 30-100 μmin width and depth. Cross sectional area of 0.01 to 0.9 are considered to be large and correspond to channels of 100-300 μmin width and depth. In one embodiment, the cross-section of the common microfluidic channel varies along the length of the channel.

In one embodiment, the apparatus is configured to provide a flow rate of the sample stream of particulate fluid of 0.1-100 μL per minute.

In one embodiment, the apparatus is configured to provide a flow rate of the guidance stream of fluid of 1-1000 μL per minute.

In one embodiment, the detection zone of the microfluidic chip comprises at least two optical waveguides, at least one of these is coupled (or configured to be coupled) to a light source and the other one is coupled or configured for coupling) to an optical detector to detect optical signal resulting from the particulates and such optical signal is measured in conjunction with the electrical signal detected at the detection electrode to improve the CV of the data points from a population of particulates.

In one embodiment, the apparatus of the invention is configured such that the AC signal is composed of at least two different frequencies and is applied to the excitation electrodes, and the detection electrodes detect impedance change caused by single passing particulates at these very same frequencies and a particulate is attributed to X or Y sub-population on the basis of amplitude and phase signals detected at the detection electrodes at each of these frequencies.

In one embodiment, the particulates are cells having different phenotypes and in which the apparatus is configured to sort the cells according to phenotype.

In one embodiment, the particulates are cells of at least two different cell types.

In one embodiment, the particulates are cells of the same type having at least two different phenotypes.

In one embodiment, the electrodes have a thickness of 0.10-300 μm.

The invention also provides an on-chip method of focussing a stream of particulate containing fluid that employs a microfluidic chip or apparatus of the invention. In one embodiment, the method comprises the steps of:

pumping a particulate containing fluid through the sample microfluidic channel;
simultaneously pumping a guidance fluid into the guidance microfluidic channel,
whereby the fluids merge to form a composite fluid stream containing a focussed beam of particulates that is disposed asymmetrically in the common microfluidic channel.

In one embodiment, the method includes an additional step of on-chip analysis of the composite fluid stream in the common microfluidic channel using one or more sensors disposed in a detection zone of the common microfluidic channel, for example, optical and/or or electrical sensing methods (described herein).

In one embodiment, the method includes an additional step of on-chip separation of particulates in the composite fluid stream in the common microfluidic channel using a suitable particulate separator. Thus, the composite stream may be separated into two or more stream characterised by particulate content (i.e. having different populations of particulate). Typically, the on-chip separation step is coupled to the on-chip analysis step whereby separation of particulates is performed in response to the on-chip analysis. In one embodiment, the particulates are sperm cells, whereby the method performs separation of the sperm cells into two populations according to sex.

Other aspects and preferred embodiments of the invention are defined and described in the other claims set out below.

DETAILED DESCRIPTION OF THE INVENTION

Figure 1A:
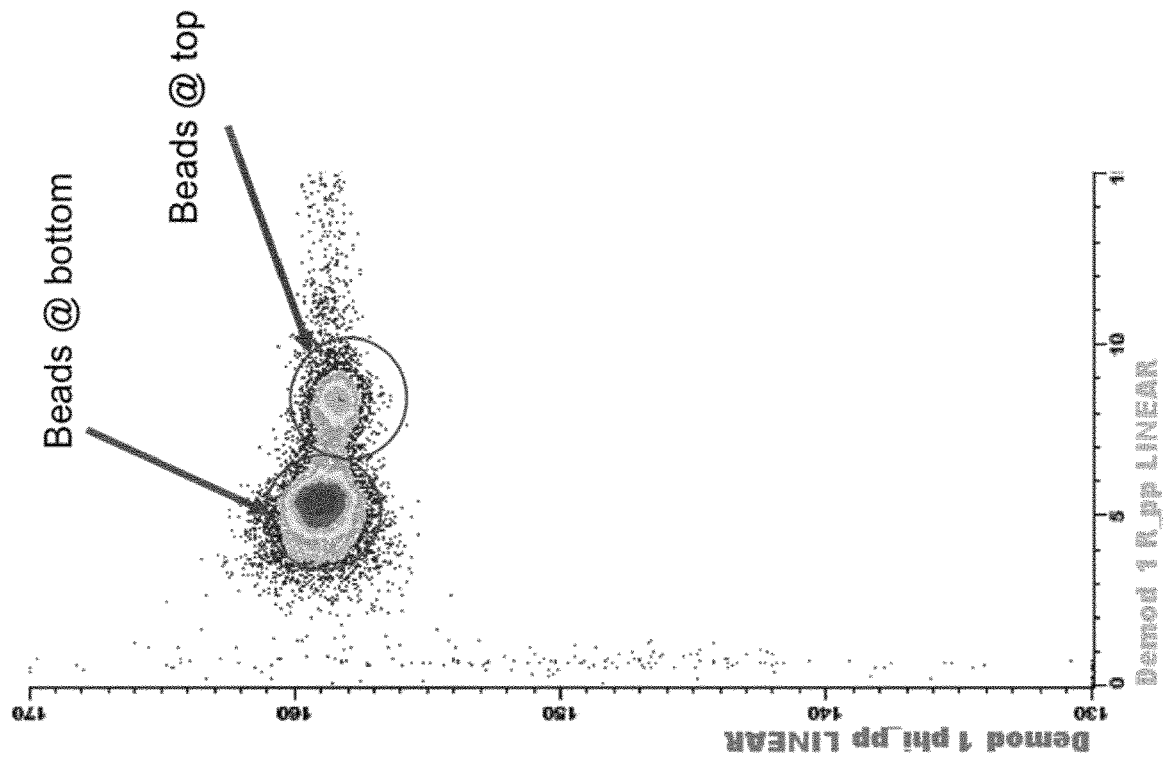
FIG. 1a Density plot of impedance magnitude versus impedance phase for a population of identical polystyrene beads suspended in phosphate saline buffer.
Figure 1A:
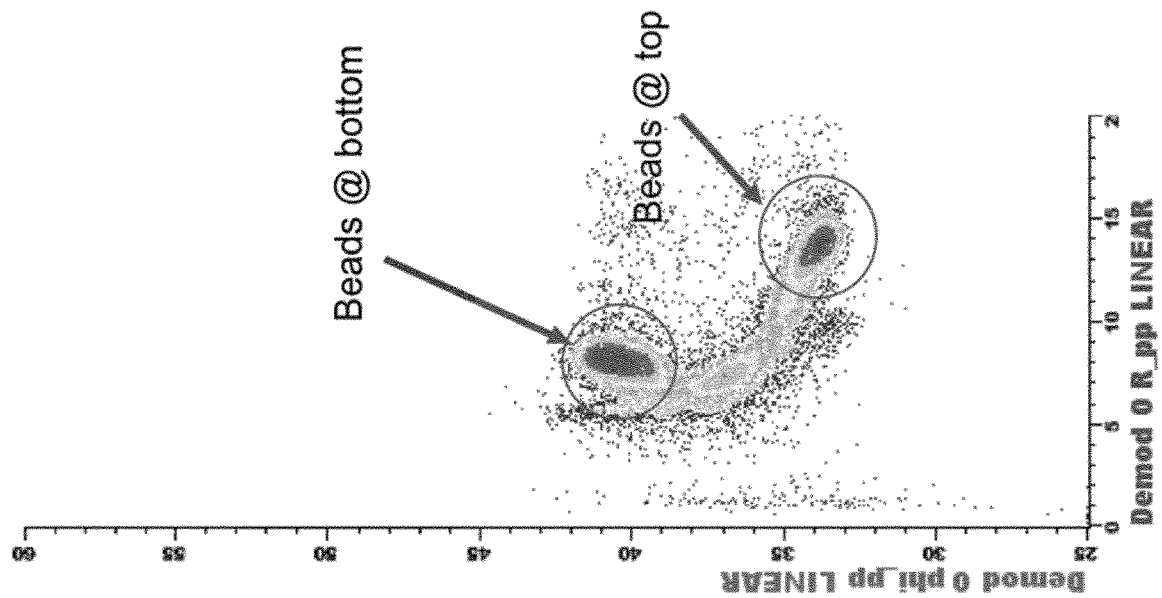
Figure 1:
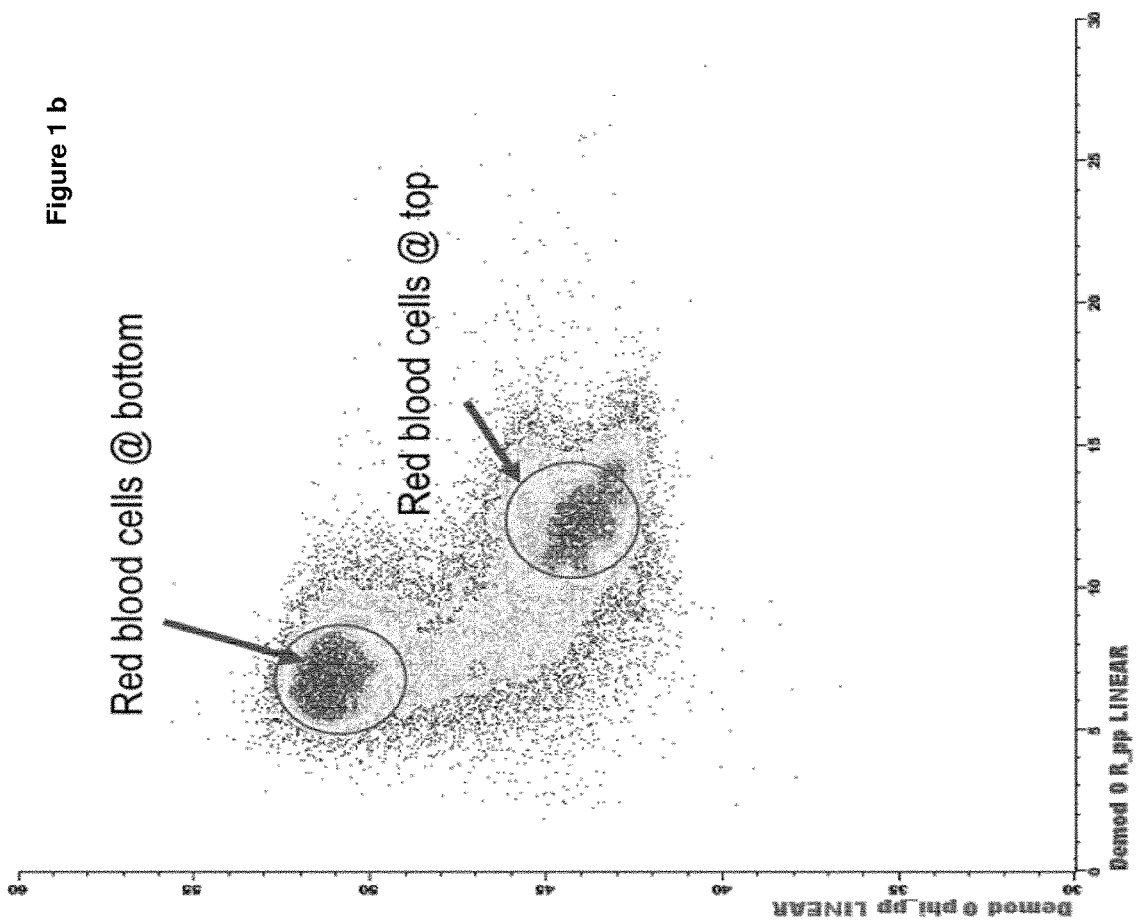
FIG. 1b Density plot of impedance magnitude versus impedance phase for a population of red blood cells suspended in phosphate saline buffer.
Figure 1:
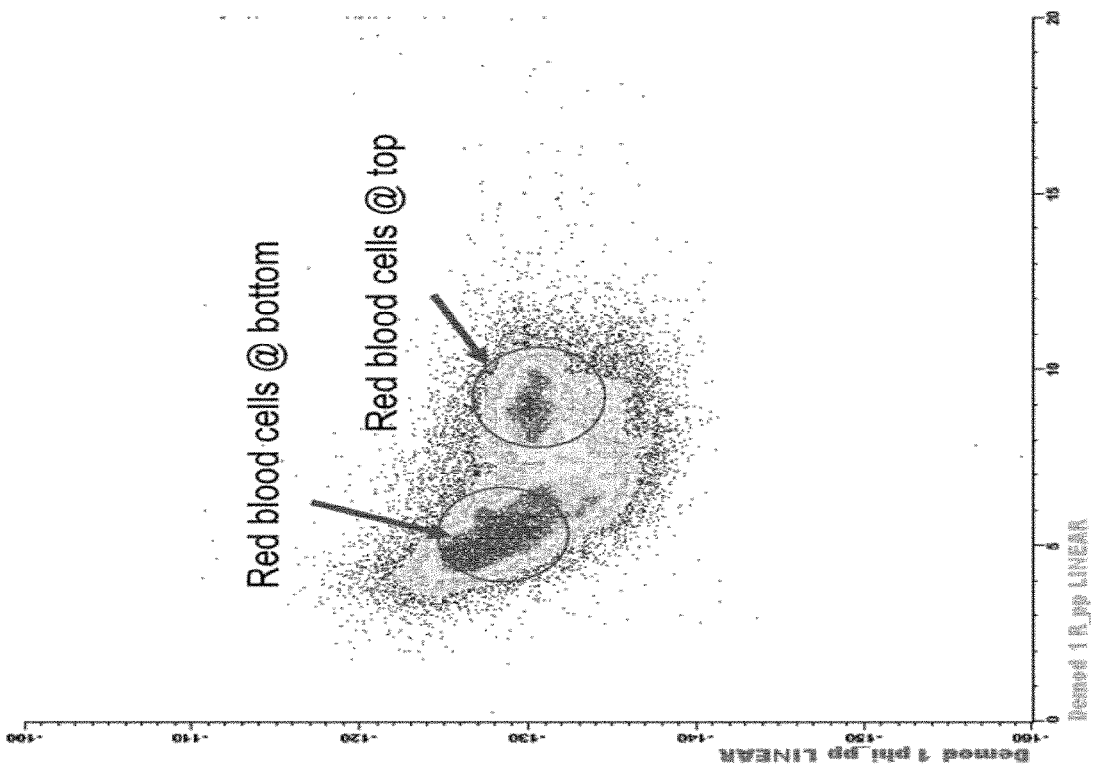

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

"Along only part of one or more sides of the guidance microfluidic channel" as applied to the merging of the sample and guidance microfluidic channels means that the sample channel merges along only part of one or more sides, and not a full side, of the guidance channel, for example along only part of one side or only part of two adjacent sides of the guidance channel. This is illustrated in most of the figures, where the merging occurs along only part of one, or two adjacent sides, of the guidance channel. This geometry forces the particulates in the common channel into a focussed beam at a hydrodynamically favoured focal point in the cross-section of the common channel, where the focussed beam is stable and resistant to de-focussing, such that the particulates pass the detection zone in the focussed beam where the statistical spread of data measured from the particulates is reduced.

"Oblique angle" as applied to the merging of the sample and guidance microfluidic channels means an angle of from 5° to 60° between longitudinal axes of the sample and guidance channels just proximal of the point of merging. In one embodiment, the oblique angle is from 05 to 45°. In one embodiment, the oblique angle is from 5° to 30°. In one embodiment, the oblique angle is from 5° to 20°.

"Particulate" as applied to a particulate containing fluid means a solid body in the fluid or a semi-solid, i.e. a body with properties different to that of the fluid. Examples include particles of metals, oxides, nitrides, sulphides, polymer particles, particles of inorganic or organic materials, particles of gel, also composite particles, and mixed particles, nano-particles, microparticles, particulate complexes, cells, bacteria, fungi, virus. Likewise, "particulate containing fluid" means a fluid containing particulates. Examples include cell containing fluids, such as sperm containing fluid.

"Disposed asymmetrically in the common channel" as applied to the focussed beam of particulates means that the focussed beam is positioned outside the geometrical centre of the cross section common channel or outside the centre of symmetry of the common channel. The focussed beam generally has a longitudinal axis that is parallel to a longitudinal axis of the common channel. When the common channel is rectangular, the geometrical centre means a point in the cross section of the channel that is equidistant from each corner. When the cross-section of the common channel is not rectangular, i.e. other polygons, the geometrical centre refers to the centroid (https://en.wikipedia.org/wiki/Centroid), geometrical centre could alternatively be interpreted as centre of mass of the area representing the cross-section of the common channel. In one embodiment, the term "disposed asymmetrically" means disposed adjacent a corner or side of the cross section of the channel.

"Hydrodynamically favoured position" as applied to the focussed beam of particulates formed in the common microfluidic channel means a position in the cross-section of the common channel in which the focussed beam is stable and unlikely to be de-focussed along the length of the common channel, alternatively, it could be defined as position/positions within the cross-section of the common channel to which the particles are guided by the balance of forces acting on the particles in the flow. The key forces acting on particles in the flow are listed earlier. It is an important point of this invention that usually there are several hydrodynamically favoured positions within a channel. Examples of hydrodynamically favoured positions include positions close to the corners and sides of polygonal cross-sectioned channels, towards the top of the common channel (when the particulates are less dense that the fluid containing the particles), or towards the bottom of the common channel (when the particulates are more dense that the fluid containing the particles). The hydrodynamically favoured positions may differ from chip to chip depending on a number of variables, including the cross-sectional shape of the common channel, the flow rates of the fluid streams, and the types of particulates, the difference between the densities of the particles and the fluid.

"Analysis" means determining a qualitative or quantitative characteristic of the particulates in the fluid, for example determining whether the particulates are a homogenous population or a heterogenous population, determining the amount or concentration of particulates, or differentiating or sorting the particulates based on differences. Thus, the term broadly covers analysis of the particulates (i.e. cells) qualitatively or quantitatively, or differentiation or sorting of the particulates based on detected impedance response differences.

"Cells" means any type of cell, including mammalian cells such as sperm, white blood cells, red blood cells, bone marrow cells, immune cells, epithelial cells, nerve cells, pulmonary cells, vascular cells, hepatic cells, kidney cells, skin cells, stem cells, or bacterial and fungal cells and hybridomas. Generally, the particulate containing fluid contains at least two different types of particulates, for example different cell types, sperm of different sex, sub-populations of the same cell types, the same cell type having different phenotypes, dead and living cells, diseased and non-diseased cells, immature and mature cells of the same kind. The apparatus and methods of the invention may be employed to analyse and/or differentiate and/or separate these different types or phenotype of particulates/cells.

"Different phenotypes" as applied to cells means different populations of cells (i.e. hepatic cells and vascular cells), different sub-populations of the same cell type (i.e. different types of cartilage cells), different phenotypes of the same cell type (i.e. cell expressing different markers, diseased and healthy cells, transgenic and wild-type cells, stem cells at different stages of differentiation).

"X and Y population" as applied to sperm cells means male sperm and female sperm cells. "Focussed stream of particulate containing fluid" means a fluid containing particulates in the form of a focussed beam of particulates asymmetrically positioned within a guidance stream. In one embodiment the particulates in the focussed beam are focussed into a single cell stream arrangement. In one embodiment, in which the particulates have an anisotropic shape, particulates in the focussed beam are aligned in the same direction.

"Microfluidic chip" means a chip having at least one microfluidic channel having a cross-sectional area of less than 1 mm$^2$ and a length of at least 1 mm. In one embodiment, the microfluidic chip has at least one microfluidic channel having a cross-sectional area of less than 0.25 mm$^2$. In one embodiment, the microfluidic chip has at least one microfluidic channel having a cross-sectional area of less than 0.01 mm$^2$. In one embodiment, the microfluidic chip has at least one microfluidic channel having a cross-sectional area of less than 0.0025 mm$^2$. In one embodiment, the microfluidic chip has a plurality of microfluidic channels, for example at least 2, 3, 4, 5, 6, 7, 8, 9 or 10 microfluidic channels. In one embodiment, the microfluidic chip has at least one microfluidic channel having a length of at least 1.500 mm. In one embodiment, the microfluidic chip has at least one microfluidic channel has a length of at least 2 mm. In one embodiment, the microfluidic chip has a length of at least 3 mm. In one embodiment, the microfluidic chip comprises a plurality of layers, for example at least 2, 3, 4, 5, 6, 7, 8, 9 or 10 layers.

"Substantially orthogonal microfluidic channel" means that the microfluidic channel runs through the chip as opposed to parallel to the layers of the chip. The channel may be perpendicular to the layers of the chip, or run through the layers of the chip at an angle, for example at an angle of 60° or 70° to a longitudinal axis of the layers of the chip.

"AC impedance changes" should be understood to mean changes in impedance detected at the detection electrode. The changes may include changes in amplitude, phase, or amplitude and phase of the signal.

"In electrical communication with the microfluidic channel" as applied to the electrodes means that the electrodes are in direct contact with the fluids analysed in the microfluidic channel.

Figure 7:
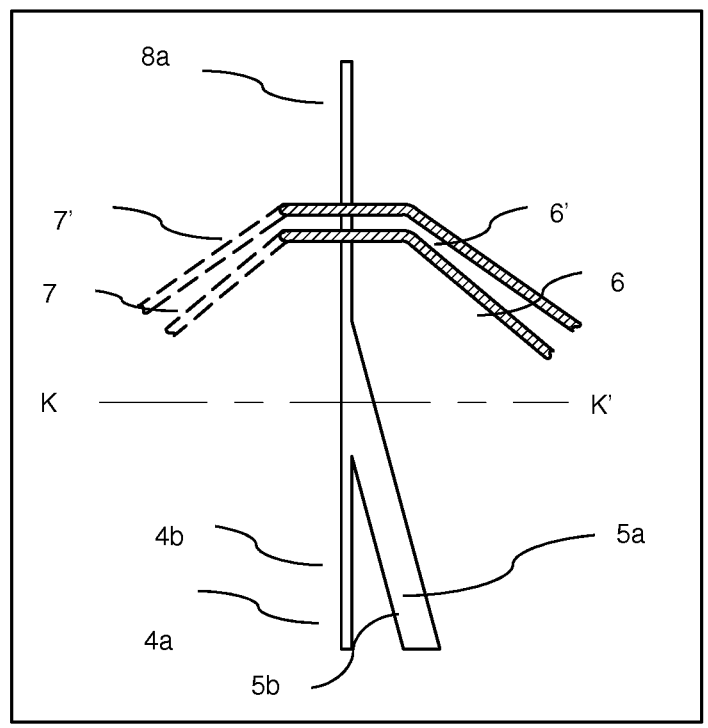

"Detection plane" means a cross-section of the microfluidic channel at which an electrode pair is located. The apparatus of the invention allows for a plurality of electrode pairs to be disposed at the same detection plane (as shown in FIG. 7), where the electrode pairs are spaced apart radially around the channel in the same plane. It also allows for a plurality of electrode pairs to be provided at different detection planes (see for example FIG. 8), where the electrode pairs are spaced apart axially along the channel.

"Separation zone" is a part of the microfluidic chip, distal of the detection zone, where particulates in the fluid can be separated based on the AC impedance changes in the channel caused by the particulates and in accordance with the results of the characterization of the particulates in the detection zone. The separation zone generally includes a force generator operably connected to the electrode pair and configured to exert a force on the particulates in response to signals from the detection zone, to separate the one or more particulates from the stream of fluid. Examples of suitable force generators for use in cell sorting apparatus are well known in the art and described for example in [15]. In one embodiment, the apparatus will typically include a processor operably connected to the at least one electrode pair and the force generator, and configured to actuate the force generator in response to a signal received from the electrode pair. The actuating signal may be pre-programmed into the processor, and may vary from cell type to cell type.

The term "anisotropic" refers to being not spherical in overall symmetry of particle's shape or its response to the stimulus used in the apparatus. In the simplest case, this refers to overall shape of the particle (cell). For example, if the particle is elongated, ellipsoidal, bar-shaped or disk-shaped, discoid, this is then described as anisotropic in contrast to a spherical shape particle that is being described as isotropic. However, the overall shape in its own right is insufficient to distinguish between anisotropic and isotropic particles (cells). For example, if a conducting rod (segment of wire) is embedded into an insulating sphere, this forms an anisotropic particle even if the overall shape of the particle is spherical, i.e. isotropic. The reason is that such a particle has different response to the Radio Frequency (RF) electromagnetic field depending on whether it is directed with the length of the rod along the field or perpendicular to the field. The main response to the RF field will be in this case from the metallic rod, this response will be highly anisotropic, the insulating spherical envelope will have little effect on the situation. The same applies to optical response: it will be different depending on the direction of the light incidence and the polarization with respect to the long axis of the rod, again the effect of the isotropic dielectric envelope on the optical response will not alter anisotropic response from the conducting rod. The same applies to the cells. The main contribution to RF signal response from a cell may not come from the exterior periphery of the cell but from its interior features. This depends on the structure of the cell and the RF frequency.

When referring to laminar flow regime, we shall imply the flow conditions that fall under the Stokes regime (~1<Re<~1000). Re is the Reynolds number defined as Re=$\rho$UH/$\mu$, where $\rho$, U and $\mu$, are the fluid density, the average velocity and dynamic viscosity respectively and H is the characteristic channel dimension. In some cases the effect of particle focusing may still be achieved when Reynolds number is below 1 and therefore the invention is not restricted to the situation of ~1<Re<~1000. Generally the range of Re values at which the focusing is achieved, also depends of the difference between the densities of the liquid and the density of the particles. The greater is the difference, e.g. the heavier are the particles compared to the liquid, the greater is the effective gravity force (difference between the gravity force and the buoyance force) pulling the particles down from the locations defined by the hydrodynamic forces. Therefore, the greater is the difference between the densities, the greater should be the force bringing the particles towards hydrodynamically favored positions to achieve effective focusing of the particle's trajectories.

This invention relates to the field of microfluidic flow cytometry and more generally microfluidic techniques for analysis of particulate-containing fluids. It deals with the improvements to such techniques in order to identify subsets of particles or sub-populations of cells that differ by their properties, and separate the said identified sub-populations of cells or subsets of particles, if so required. In particular, the invention deals with a microfluidic chip, whereby the stream of particles or cells is positioned within a cross-section of the microfluidic channel in a controlled way to reduce a variation of detected signal and thus make distinction between subsets of cells or particles, more robust. The invention teaches that locations exist within the channel of a detection zone of microfluidic chip at which the statistical spread of the data measured from a set of cells or particles, is reduced under suitable hydrodynamic conditions. This reduction is achieved by a more tightly focused flow of particles (cells) within the channel and also by a more homogeneous alignment of the particles (cells) within the channel. The latter is particularly useful if the particles (cells) are not circular in shape, e.g. elongated, elliptical or discoid. The invention also teaches how to guide the cells or particles through such preferable locations and the hydrodynamic conditions at which the focusing of particles could be achieved. Several geometries of the microfluidic chip are suggested, that use the guidance fluid to direct the particulate containing fluid into such locations within the channels where the variation in the signal spread from individual cells or particles is reduced and identification of the sub-sets of particles (cells) is achieved more readily. We describe an embodiment of this invention where the identification of the particles/cells is done using impedance spectroscopy. Other methods of cells identification, e.g. fluorescence detection or optical scattering, can also be used with the invention.

Broadly, the invention provides a microfluidic chip for positioning of particles of a particulate-containing fluid comprising means for merging the flows of the particulate-containing fluid and a guidance fluid in a single common channel in such a way that the trajectory of particulate-containing fluid in the detection zone of the common channel is guided by the guidance fluid to pass through a hydrodynamically favoured position for the particles within the common channel, at such a position the trajectories of individual particles are bundled into a focused beam of near straight lines by the forces acting on particles in the laminar flow in the common channel.

Typically, the hydrodynamically favoured position is located substantially outside the geometrical centre of the common channel. Suitably, the hydrodynamically favoured position is in the vicinity of one or several corners of the common channel and the common channel is of a rectangular shape. In one embodiment, the hydrodynamically favoured position is located in the vicinity of the middle points of some of the sides of the common channel and the common channel is substantially of a rectangular or a square cross-section. In one embodiment, the common channel is of a rectangular cross-section with the width being substantially greater than the height and the hydrodynamically favoured position is located close to one of the centres of the longer sides of the rectangle forming the interior of the common channel cross-section. In one embodiment, the particulate-containing fluid and guidance fluid are merged in a substantially non-symmetric fashion so that particulate containing fluid is injected into the flow of guidance fluid in a substantially asymmetric fashion. In one embodiment, the particulate containing fluid is injected close to such a point in the cross-section of the common channel that projects on to the hydrodynamically favoured position within the common channel by following the lines of fluid flow in the common channel from the point of injection of the particulate containing fluid to the detection zone within the common channel.

In one embodiment, the particulate-containing fluid flow is merged with the guidance fluid by injecting the particulate-containing fluid at the peripheral point of the cross-section of the channel carrying the guidance fluid. In one embodiment, the hydrodynamically favoured position is selected from several such possible hydrodynamically stable positions within the cross-section of the channel so that the hydrodynamically favoured position is located in the lower part of the channel for the analysis of particulate containing fluid provided that the particles (cells) have greater density than the density of the particulate containing fluid, and is located in the upper part of the channel provided that the particles (cells) have smaller density than the density of the particulate containing fluid; and the guidance fluid flow is arranged in such a way that the particles (cells) are guided towards the selected hydrodynamically favoured position. In one embodiment, the channel of the guidance fluid has a rectangular cross-section. In one embodiment, the particulate fluid flow is injected close to one of the corners of the channel of the guidance fluid. In one embodiment, the particulate fluid flow is injected close to the centre of one of the sides of the channel carrying the guidance fluid. In one embodiment, the particulate fluid is injected away from the centre of the channel carrying guidance fluid.

In one embodiment, there are multiple hydrodynamically favoured positions for the particles in the common channel and the flow of guidance fluid guides the particles towards a subset of the hydrodynamically favoured positions in the common channel, away from other such hydrodynamically favoured positions.

In one embodiment, the chip is used for identification of the particles (cells) using impedance spectroscopy and the particles guided by the guidance fluid, pass through a detection zone with electrodes; of these electrodes at least one is the excitation electrode and at least one is the detection electrode.

In one embodiment, the excitation electrode (electrodes) are excited at at least two different frequencies in the range of 0.1 to 200 MHz and the signals are measured at the detection electrodes at these very frequencies.

In one embodiment, the signal measured at the detection electrode is a complex signal comprising both, the amplitude and the phase characteristics of the detection signal.

In one embodiment, the guidance fluid directs particles (cells) in a uniform fashion with respect to the electrodes of the detection zone.

In one embodiment, the guidance fluid directs the particles (cells) to such a trajectory within the detection zone of the common channel that particles (cells) pass parallel to the electrodes and the separation distance from the particles to the electrodes at these trajectories is kept nearly the same for all the particles as their trajectories are on the line of hydrodynamically favoured positions for the particles in the common channel.

In one embodiment, the particles are anisotropic in shape, and the hydrodynamically favoured position is chosen in the vicinity of at least one wall of the channel so that the effect of the wall and hydrodynamic flow forces rotate particles to align them in the same orientation with respect to the electrodes.

In one embodiment, the separation of particles (cells) follows their identification in the detection zone and such separation takes place in the separation zone at which cell arrive after exiting the detection zone.

In one embodiment, the hydrodynamically favoured position is located close to one of the four four of the common channel. In one embodiment, the hydrodynamically favoured position is located close to one of the four corners of the common channel.

In one embodiment, the hydrodynamically favoured position is located close to one of the four sides of the common channel and the common channel is of substantially rectangular or square cross-section.

In one embodiment, the hydrodynamically favoured position is defined by the geometry of the channel, flow rate and characteristics of the particles including their density, size and characteristics of the particulate-containing fluid and the guidance fluids including their densities and viscosities.

The invention also provides a microfluidic chip for identification of particles of a particulate-containing fluid using impedance spectroscopy, such chip transporting the particles through a common channel towards the detection zone having electrodes; of these electrodes at least one is the excitation electrode and at least one is the detection electrode; where such a chip further comprises means for merging the flows of the particulate-containing fluid and a guidance fluid in a single common channel in such a way that the trajectory of particulate-containing fluid in the detection zone of the common channel is guided by the guidance fluid to pass through a hydrodynamically favoured position for the particles within the common channel, where the trajectories of individual particles are bundled into a focused beam of near straight lines by the forces acting on particles in the laminar flow in the common channel and the flow of guidance fluid guides the particles towards some subset of the hydrodynamically favoured positions in the common channel, away from other such hydrodynamically favoured positions; and such positions to which the particles are guided, are located closer to the excitation electrodes than other hydrodynamically favoured positions within the common channel.

In one embodiment, the excitation electrode (electrodes) are excited at two or more different frequencies in the range of 0.1-200 MHz and the signals are measured at the detection electrodes at these very frequencies.

In one embodiment, the signal measured at the detection electrode is a complex signal comprising both, the amplitude and the phase characteristics of the detection signal.

In one embodiment, the particles are anisotropic in shape, and the hydrodynamically favoured position is chosen in the vicinity of at least one wall of the channel so that the effect of the wall and hydrodynamic flow rotates particles to align them preferentially in the same orientation with respect to the electrodes.

The invention also provides a microfluidic chip for positioning of particles of a particulate containing fluid comprising means for merging the flows of the particulate-containing fluid and a guidance fluid in a single common channel in such a way that the trajectory of particulate-containing fluid in the detection zone of the common channel is guided by the guidance fluid to pass through a hydrodynamically favoured position for the particles within the common channel, where the trajectories of individual particles are bundled into a focused beam of near straight lines by the forces acting on particles in the laminar flow in the common channel; and optical detection is used for the identification of the particles.

In one embodiment, the hydrodynamically favoured position is located substantially outside the geometrical centre of the common channel.

In one embodiment, the hydrodynamically favoured position is in the vicinity of one or several of the corners of the common channel and the common channel is of a rectangular shape.

In one embodiment, the hydrodynamically favoured position is located in the vicinity of the middle points of some of the sides of the common channel and the common channel is of a rectangular or a square cross-section.

In one embodiment, the common channel is of a rectangular cross-section with the width being substantially greater than the height and the hydrodynamically favoured position is located close to one of the centres of the longer sides of the rectangle forming the interior of the common channel cross-section.

In one embodiment, the particulate-containing fluid and guidance fluid are merged in a substantially non-symmetric fashion so that particulate containing fluid is injected into the flow of guidance fluid in a substantially asymmetric fashion.

In one embodiment, the particulate-containing fluid flow is merged with the guidance fluid by injecting it at the peripheral point of the cross-section of the channel carrying the guidance fluid.

In one embodiment, the particulate containing fluid is injected close to such a point in the cross-section of the common channel that projects on to the hydrodynamically favoured position within the common channel by following the lines of fluid in the common channel from the point of injection of the particulate containing fluid to the detection zone within the common channel.

In one embodiment, the particles are anisotropic in shape, and the hydrodynamically favoured position is chosen in the vicinity of at least one wall of the channel so that the effect of the wall and hydrodynamic flow forces rotate particles to align them in the same orientation with respect to the incoming optical beam of the detector.

The invention also provides a microfluidic chip for positioning and alignment of particles of a particulate-containing fluid; such particles being anisotropic in shape; comprising means for merging the flows of the particulate-containing fluid and a guidance fluid in a single common channel to form a focused beam of lines of the particles trajectories by the forces acting on particles in the laminar flow in the common channel where the direction of the alignment of particles' short axes in the case of discoid particles or long axis in the case of elongated particles; is along the boundary separating the body of particulate-containing fluid from the body of guidance fluid in the common channel In one embodiment, the particulate-containing fluid and guidance fluid are merged in a substantially non-symmetric fashion so that particulate containing fluid is injected into the flow of guidance fluid in a substantially asymmetric fashion.

In one embodiment, the particulate-containing fluid flow is merged with the guidance fluid by injecting the particulate-containing fluid at the peripheral point of the cross-section of the channel carrying the guidance fluid.

This invention tackles the problem of variability of signal in a microfluidic flow cytometer or particle analyzer. It teaches the way of hydrodynamically focusing particles and cells within the detection channels to reduce the signal variability, provides the apparatus and method to practice the invention. Contrary to the conventional three-dimensional hydrodynamic focusing used with microfluidic chips where the flow of particles is focused at the center of the channel, the invention suggests that particles/cells should not be focuses into the center of the detection channel. In contrast to the prior art we use sheath stream in order to focus particles into the corners of the flow channel, where their position is stable under the correctly suitable conditions of laminar flow. Our apparatus and method take into account stable hydrodynamic positions of particles due to the inertial lift forces and therefore provide more stable focusing than used in prior art technologies.

The invention also provides a microfluidic chip for identification of particles of a particulate-containing fluid using impedance spectroscopy, such chip transporting the particles through a common channel towards the detection zone having electrodes; of these electrodes at least one is the excitation electrode and at least one is the detection electrode; where such a chip further comprises means for merging the flows of the particulate-containing fluid and a guidance fluid in a single common channel in such a way that the trajectory of particulate-containing fluid in the detection zone of the common channel is guided by the guidance fluid to pass through a hydrodynamically favoured position for the particles within the common channel, where the trajectories of individual particles are bundled into a focused beam of near straight lines by the forces acting on particles in the laminar flow in the common channel, and wherein the flow of guidance fluid guides the particles towards some subset of the hydrodynamically favoured positions in the common channel, away from other such hydrodynamically favoured positions; and wherein such positions to which the particles are guided, are located closer to the excitation electrodes than other hydrodynamically favoured positions within the common channel.

In one embodiment, the excitation electrode (electrodes) are excited at two or more different frequencies in the range of 0.1 to 200 MHz and the signals are measured at the detection electrodes at these very frequencies.

In one embodiment, the signal measured at the detection electrode is a complex signal comprising both, the amplitude and the phase characteristics of the detection signal.

In one embodiment, the particles are anisotropic in shape, and the hydrodynamically favored position is chosen in the vicinity of at least one wall of the channel so that the effect of the wall and hydrodynamic flow rotates particles to align them preferentially in the same orientation with respect to the electrodes.

Microfluidic chip for positioning and alignment of particles of a particulate-containing fluid in which the particles are anisotropic in shape, the chip comprising means for merging the flows of the particulate-containing fluid and a guidance fluid in a single common channel to form a focused beam of lines of the particles trajectories by the forces acting on particles in the laminar flow in the common channel, where the direction of the alignment of particles' short axes in the case of discoid particles or long axis in the case of elongated particles is along the boundary separating the body of particulate-containing fluid from the body of guidance fluid in the common channel Exemplification The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 2A:
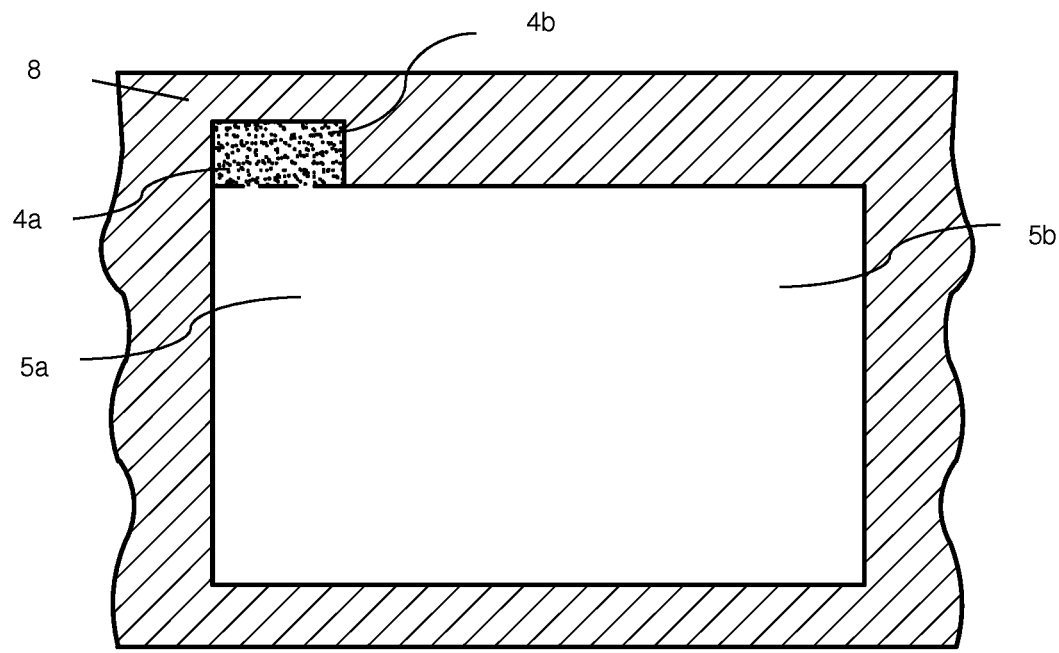
FIG. 2a Cross-section A-A' of hydrodynamic focusing microfluidic chip 8 at position of the merge of particulate containing fluid channel 4a and guidance fluid channel 5a FIG. 2b Cross-section B-B' of hydrodynamic focusing microfluidic chip 8 before position of the merge of particulate containing fluid channel 4a and guidance fluid channel 5a FIG. 2c Cross-section C-C' of hydrodynamic focusing microfluidic chip 8 before position of the merge of particulate containing fluid channel 4a and guidance fluid channel 5a FIG. 2d Cross-section D-D' of hydrodynamic focusing microfluidic chip 8 displaying common channel 8a FIG. 2e Cross-section E-E' of hydrodynamic focusing microfluidic chip 8 displaying common channel 8a FIG. 2f Cross-section F-F' of hydrodynamic focusing microfluidic chip 8 displaying common channel 8a at the detection zone FIG. 3 Top view of embodiment hydrodynamic focusing microfluidic chip 8
Figure 2B:
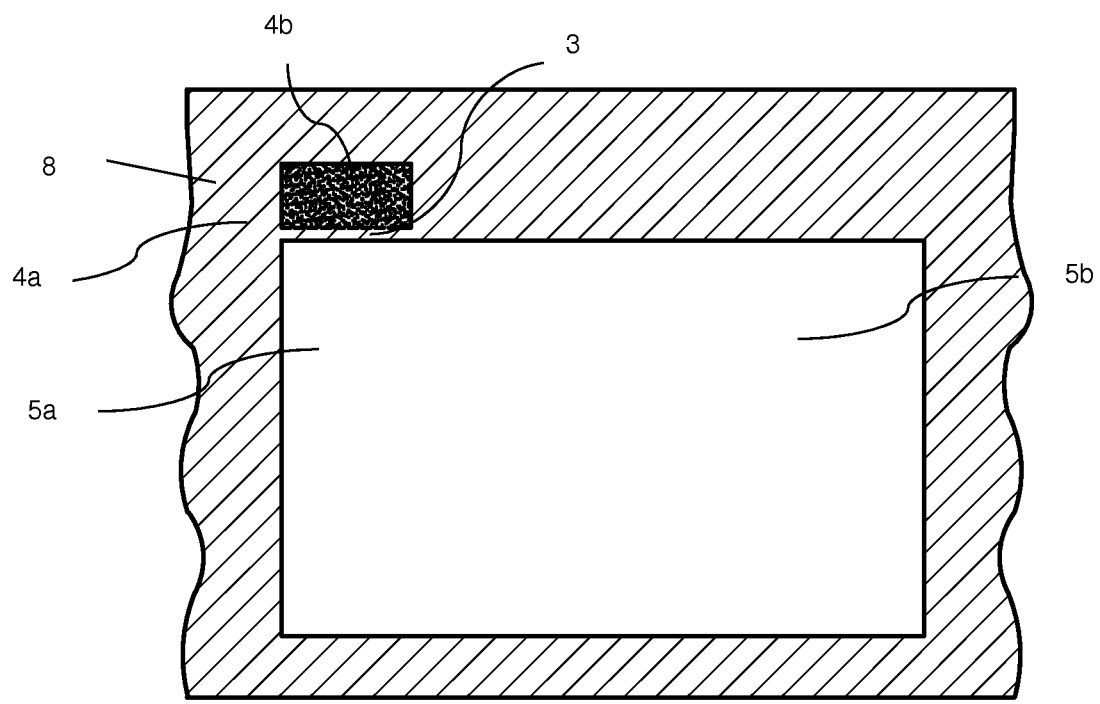
Figure 2C:
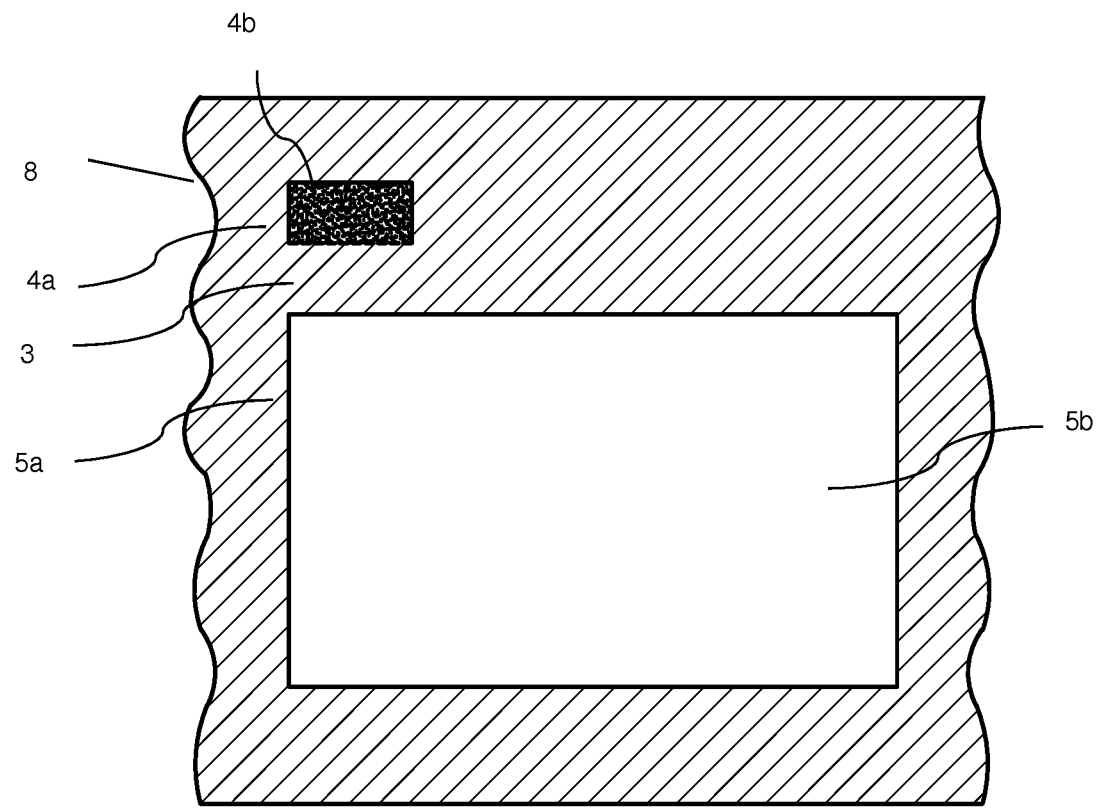
Figure 2D:
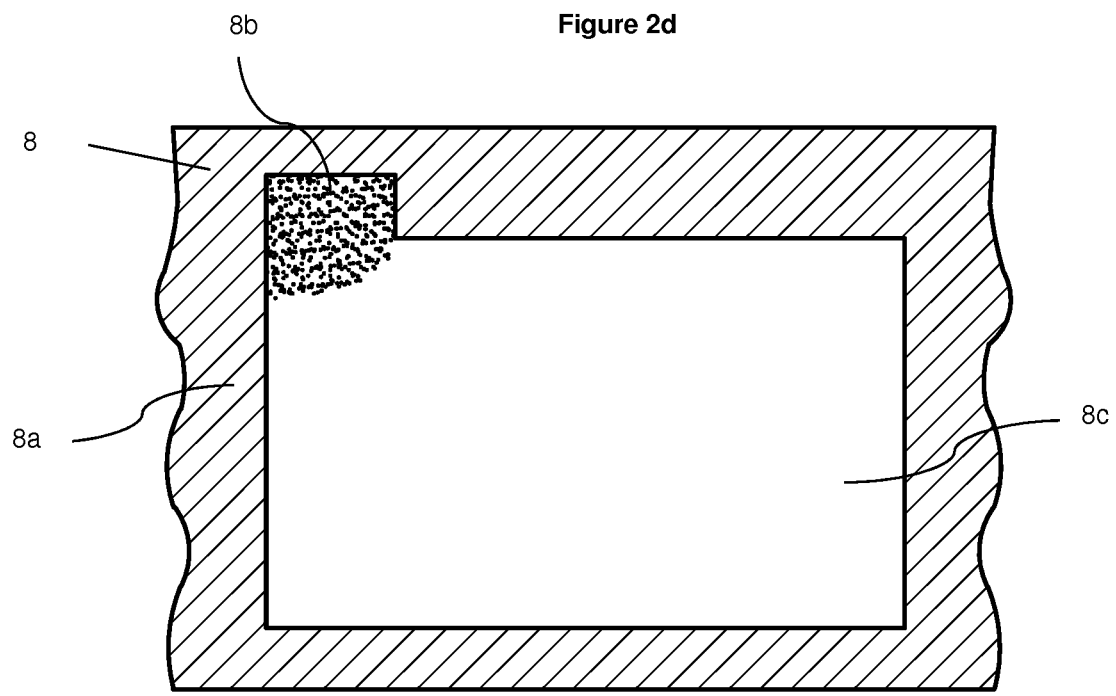
Figure 3:
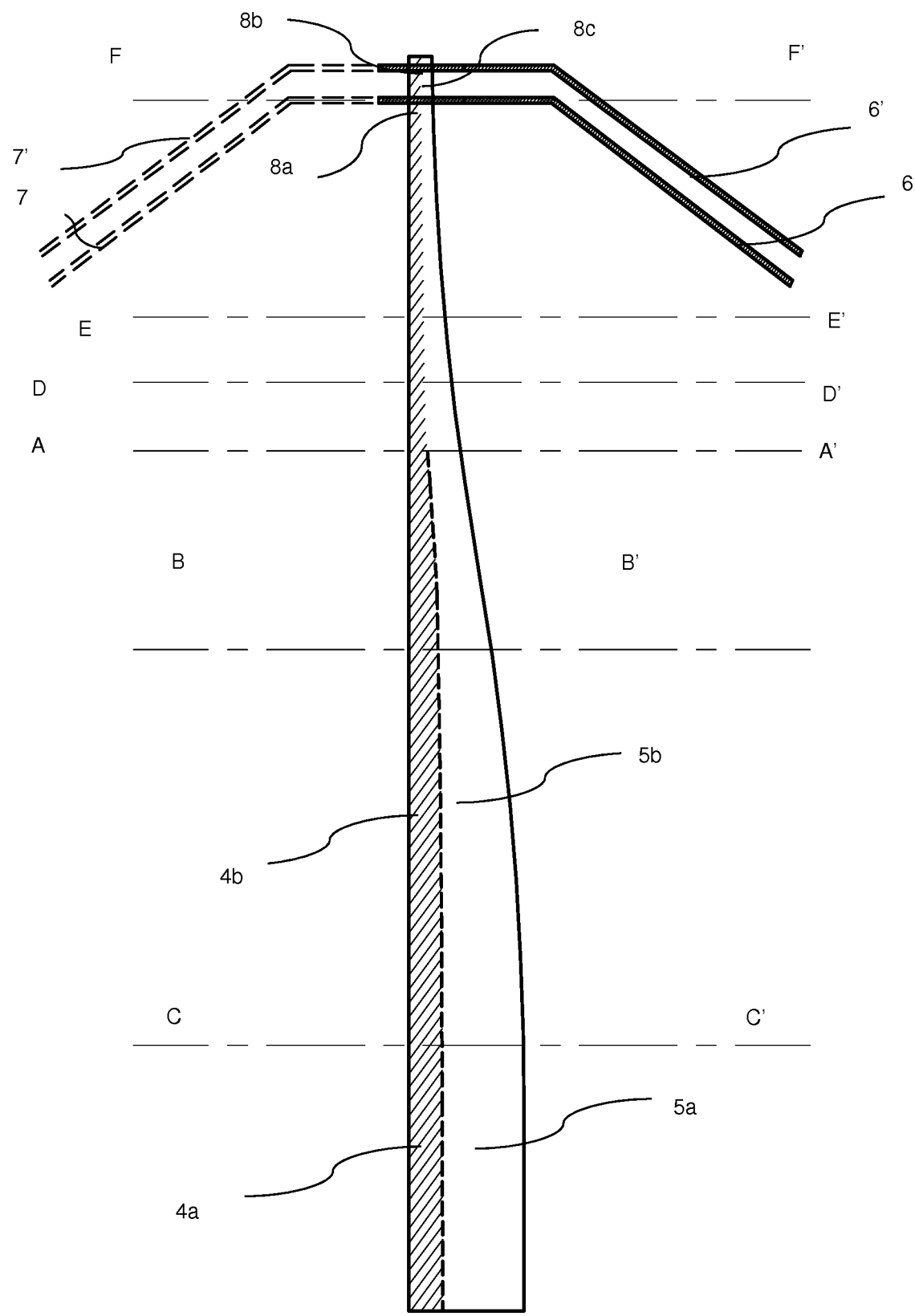

FIGS. 2a, 2b, and 2c show cross-section of the two channels: the smaller channel 4a carries the particulate containing fluid 4b and the larger channel 5a is carries the guidance fluid 5b. The guidance fluid is not shown for clarity of the drawings. The entire cross-section 5a of the channel is normally filled with the guidance fluid. The particulate containing fluid channel 4a has the cross section with the width and height in the range of 0.005-1 mm. In some special cases the width out to 10 mm could be considered if it is combined with the small height in the sub-millimeter range. The guidance fluid carrying channel 5a has the cross-section in the range of 0.05-10 mm×0.05-10 mm. The channels 4a and 5a are made out of polymer materials such as PMMA but could also be made out non-polymer materials, e.g. glass. FIG. 2a shows the two channels 4a and 5a at the point where they merge, at the cross section A-A' of FIG. 3. The wall separating the two channels indicated by numeral 3 disappears at that point and the wall position is shown with dashed line. FIG. 2c shows the two channels 4a and 5a at the cross-section C-C' of FIG. 3 where the wall 3 separating the two channels has the finite width, typically in the range of 0.005-1 mm. FIG. 2b shows the two channels 4a and 5a at the cross-section B-B' of FIG. 3. At that point the wall 3 is thinner than in FIG. 2c but it is still present. The top view of the fragment of the apparatus is shown in FIG. 3. The two channels 4a and 5a merge to form a single common channel 8a. FIGS. 2d, 2e, 2f show details of the common channel 8a at the cross-sections D-D', E-E' and F-F' respectively. The common channel 8a may have the dimensions different to the ones of the particulate fluid carrying channel 4a. The positions of the particles 4b (cells) are indicated on each channel by a cloud of dots. The common channel 8a typically has a smaller cross-section than the cumulative cross-section of the particulate containing fluid channel 4a and the guidance fluid channel 5a. The common channel 8a typically has interior width and height in the range of 0.005-10 mm. All the three channels could be fabricated on a single microfluidic chip indicated by numeral 8. The embodiment shown in FIG. 2f and in FIG. 3 also shows the electrodes of the impedance spectroscopy apparatus (excitation electrode 6 and measurement electrode 7). In this case the detection and identification of particles is based on measurements of changes to impedance due to particles passing in between the electrodes 6 and 7. The embodiment has four electrodes, two of these are located above the common channel 8a (indicated by 6 and 6') and two electrodes are below it (indicated by 7 and 7'). The channel upper and lower walls are in the range of 0.1-10 mm but typically could be around 0.5 mm. The distance from the point where the two channels merge to the location of the electrodes is typically in the range of 0.05-1 mm but could also be outside this range. The location where the electrodes 6, 6', 7 and 7' are positioned is called the detection zone. In this embodiment the hydrodynamically favored positions are at the four corners of the common channel 8a. They are marked by numerals 9a, 9b, 9c, 9d. These four hydrodynamic favored positions 9a-9d are achieved e.g. for the suspension of red blood cells in phosphate saline buffer, with the flow velocity of 0.56 msec and the size of the channel of 30 micrometers width by 30 micrometers height. When referring to the flow velocity we refer to the velocity at the center of the common channel 8a. This velocity in a laminar flow channel is greatest at the center of the channel and it declines closer to the walls of the channel. As the cross-section of the common channel 8a is reduced in comparison with the cumulative cross-section of the particulate containing fluid 4a and the guidance fluid channels 5a, the linear velocity of the fluid in the common channel 8a is much greater than the velocity in the guidance fluid channel 5a. The injection of the particulate containing fluid 4b into the upper left corner of the guidance fluid channel 5a favors position 9a over the other three positions. The favored positions of the cells are located some distance away from the walls of the common channel. The location of the favored position depends on the Reynolds number defined by the density and viscosity of the fluid, linear velocity of the flow, dimensions of the channel. For a channel 8a with the width and height of 40 micrometers and 40 micrometers respectively and the linear flow velocity in the middle of the common channel 8a of 0.3 m/s, and water-based fluid in the common channel, the favored position is located some 0.005 mm from each of the two walls forming the corner. These values scale up or down with the overall width and height of the common channel and the flow conditions. The four hydrodynamically favored positions in a common channel of a rectangular cross-section are not always equally suitable for particle analyser (cell cytometer). If the density of the particles (cells) is significantly greater than the density of the particulate containing fluid, it may be preferable to select the position at one of the lower corners of the common channel. In the opposite case when the density of particles (cells) is much smaller than the density of the particulate containing fluid, it may be advantageous to select hydrodynamically favored position at one of the upper corners of the common channel. This selection is consistent with the effect of the gravity force and buoyance force acting on the particle. If the cumulative action of these two forces is pulling the particle down, the choice of the hydrodynamically favored position close to the floor of the channel will decrease the de-focusing effect of the force. The same rationale applies to the other situation of particles (cells) having lower density than the fluid carrying them and therefore experiencing upward directed force as a cumulative action of the gravity and the buoyance. The proximity of the hydrodynamically favored position to the ceiling in this case will reduce the de-focusing effect of such gravity-originated forces. These considerations apply assuming that the chip is positioned horizontally. If the selected hydrodynamically favored position is located closer to the floor of the common channel, it may be advantageous to swap the positions of the excitation 6 and 6' and detection electrodes 7 and 7' to increase the sensitivity of the cytometer so that the excitation electrodes 7 and 7' are located closer to the particles (cells) in the channel. The relative positions of the particulate containing channel with respect to the guidance fluid channel cross-section is given by the selected hydrodynamically favored position. In this case the selected hydrodynamically favored position is at the upper left corner of the common channel and this determines that injection of the particulate containing fluid is done at the upper left corner of the guidance fluid channel. The cells come though the favored location forming tight bundle of trajectories as shown in FIG. 2f. The dimension of the cross-section of the bundle in the detection zone depend of the flow conditions such as flow velocity (flow rate), the distance from the point where the channels merge, to the detection zone and the dimensions of the common channel. However, what important in this case is that the particles (cells) could be bundled into a much tighter bundle in any of the hydrodynamically favored positions.

Figure 4:
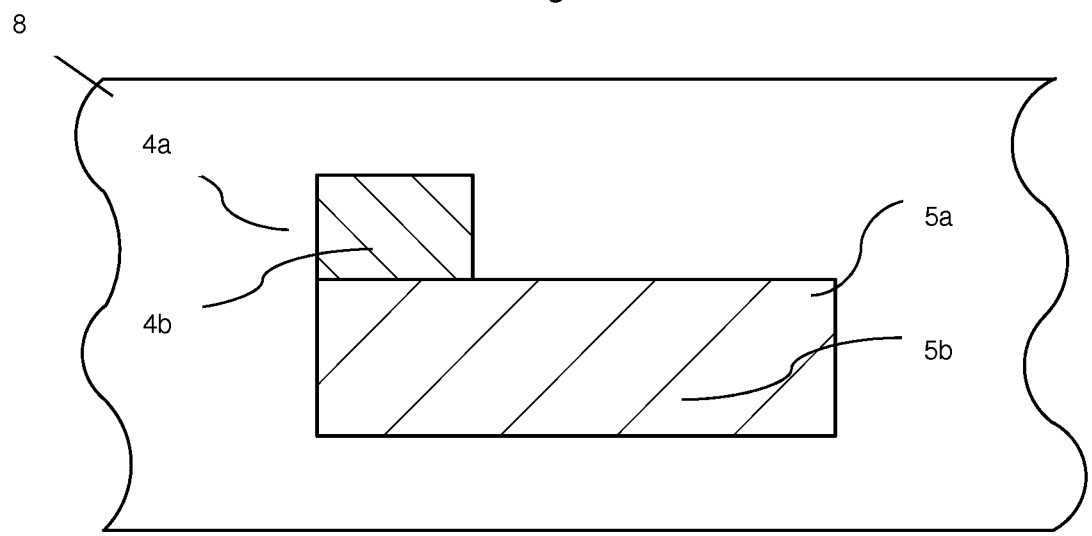
FIG. 4 Cross-section K-K' of embodiment of hydrodynamic focusing microfluidic chip 8 displaying position of merge of particulate containing fluid channel 4a and guidance fluid channel 5a FIG. 5 Top view of embodiment hydrodynamic focusing microfluidic chip 8 with particulate containing channel 4a joining from the top left.
Figure 5:
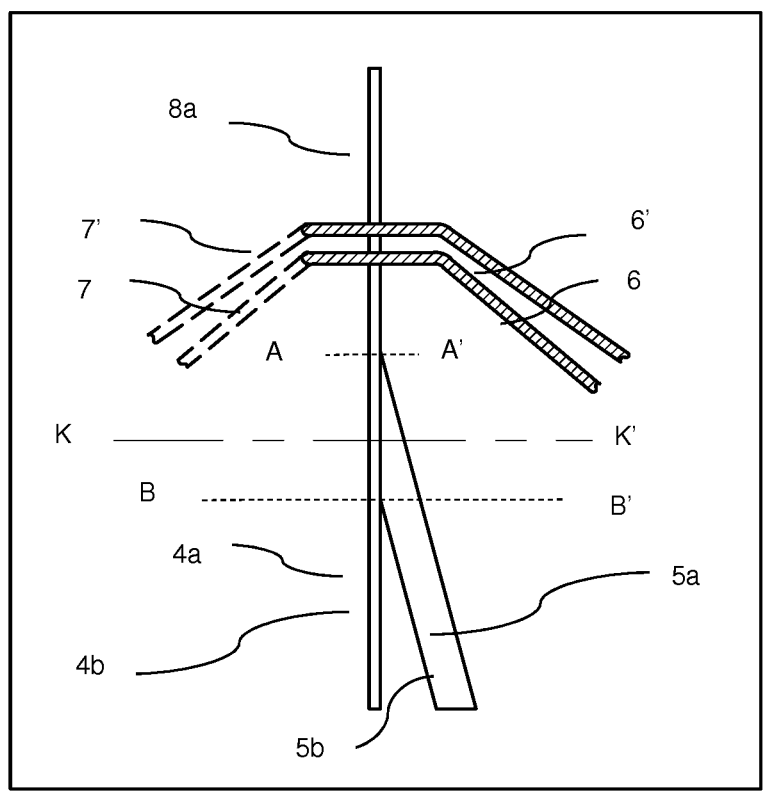

Below we describe a number of embodiments that are easier to fabricate than the embodiment presented in FIGS. 2 and 3. The first such embodiment is shown in FIG. 4 and FIG. 5. FIG. 4 corresponds to cross-section K-K' of FIG. 5. In this case the embodiment has height of the common channel 8a the same as the height of the particulate containing fluid 4a channel, which makes it easier to fabricate the chip using polymer photolithography method using SU-8 photopolymer material. The width of the common channel 8a may or may not be equal to that of the particulate containing fluid channel 4a. Embodiment in FIG. 5 shows the situation when the two widths are equal. In this way the common channel 8a is a geometrical continuation of the particulate containing fluid channel 4a along its axis. One could also device embodiments where the common channel 8a makes an angle with the direction of the particulate containing fluid 4a channel, i.e. there is a bend along the length of the common channel 8a. The guidance fluid channel 5a is directed to form the angle of 3-30 degrees with the particulate containing fluid channel 4a. In this respect the embodiment shown in FIG. 5 differs from the embodiment in FIG. 3 where the guidance fluid channel 5a is tangent to the particulate fluid channel 4a at the point of them merging, i.e. the angle between them is zero. The guidance fluid channel 5a vanishes at the point marked by a letter A on FIG. 5. The widths and heights of the guidance fluid channel 5a, particulate containing fluid channel 4a and the common channel 8a, wall thickness of the channel floor and channel ceiling, are similar to the dimensions of these indicated in reference to FIGS. 2 and 3 as well as the linear flow velocities in the channels. There is an arrangement of four electrodes 6,6',7 and 7' similar to the one in FIGS. 2 and 3. The particulate containing fluid channel 4a is located just above the guidance fluid channel 5a and, unlike in the embodiment shown in FIG. 2, there is no wall separating them which makes it easier to fabricate compared to the microfluidic chip shown in FIG. 2. The particulate fluid containing channel 4a and the guidance fluid channel 5a merge between the points B and A marked in FIG. 5. In this case the particulate containing fluid 4b is guided towards one of the four hydrodynamically favored positions located proximal to the upper left corner of the common channel 8a.

Figure 6:
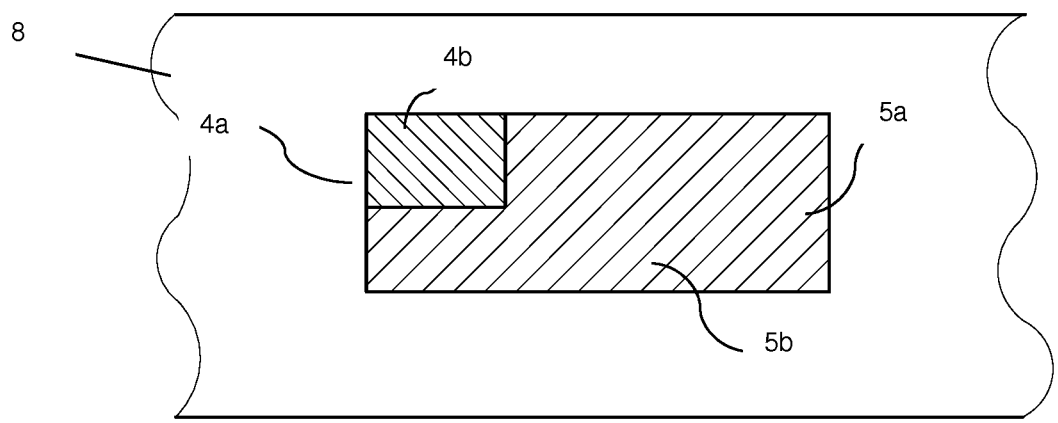
FIG. 6 Cross-section K-K' of embodiment of hydrodynamic focusing microfluidic chip 8 displaying position of merge of particulate containing fluid channel 4a and guidance fluid channel 5a FIG. 7 Top view of embodiment hydrodynamic focusing microfluidic chip 8 with particulate containing channel 4a joining from the top left and guidance fluid channel joining from the bottom right.

FIGS. 6 and 7 show another embodiment where the particulate containing fluid channel 4a enters into the guidance fluid channel 5a at its top right corner. FIG. 6 shows cross-section of the channel shown in FIG. 7 along the line K-K'. The two channels 4a and 5a are shown in FIG. 7 as separated by a solid line, however, there is no wall separating the two channels at that point. All the points related to the dimensions of the channels, the flow conditions, electrodes, manufacturability of the microfluidic chip, etc. made in relation to FIGS. 4 and 5, apply also to FIGS. 6 and 7. In this case the particulate containing fluid 4b is guided towards one of the four hydrodynamically favored positions located proximal to the upper left corner of the common channel.

Figure 8:
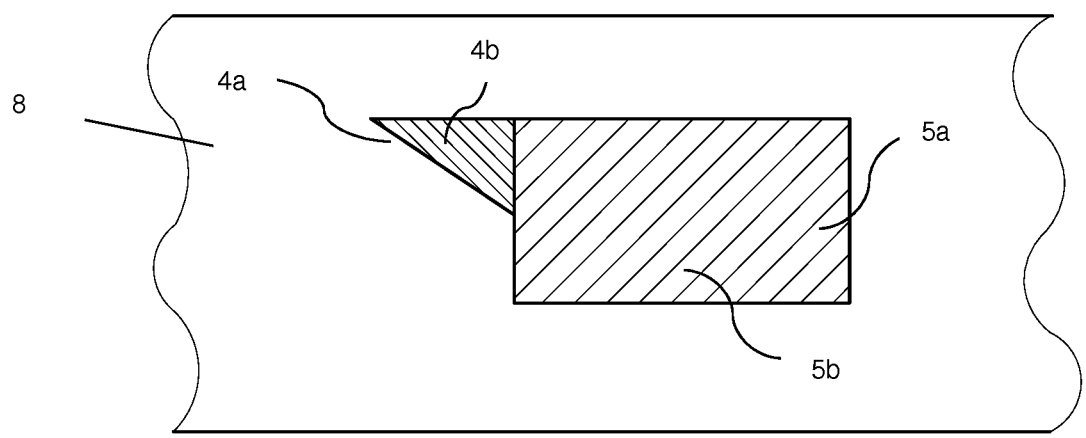
FIG. 8 Cross-section K-K' of embodiment of hydrodynamic focusing microfluidic chip 8 displaying position of merge of particulate containing fluid channel 4a and guidance fluid channel 5a, where particulate containing fluid channel 4a is triangular shape FIG. 9 Top view of embodiment of hydrodynamic focusing microfluidic chip 8 with particulate containing channel 4a of a triangular shape FIG. 10 Cross-section K-K' of embodiment of hydrodynamic focusing microfluidic chip 8 displaying position of merge of particulate containing fluid channel 4a and guidance fluid channel 5a FIG. 11 Top view of an embodiment of hydrodynamic focusing microfluidic chip 8 with particulate containing channel 4a joining from the top left and guidance fluid channel joining from the bottom right.
Figure 9:
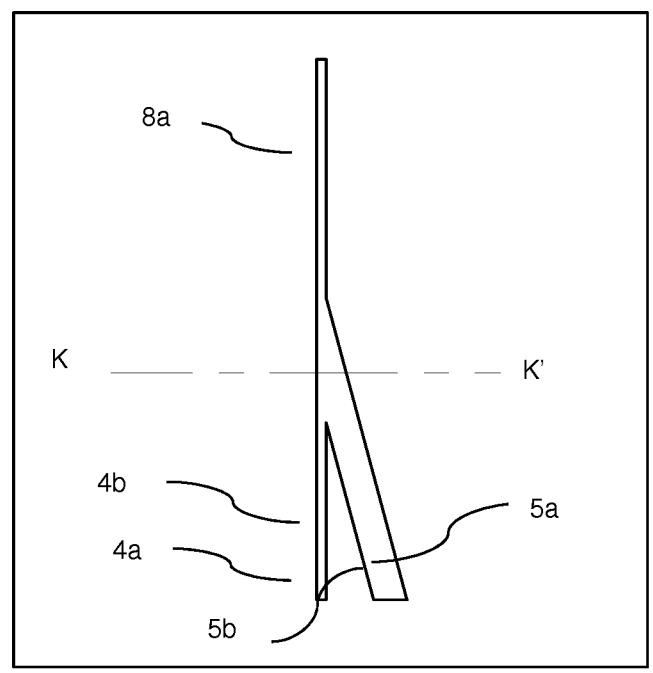

The particulate fluid carrying channel 4a and the guidance channel 5a do not have to have rectangular or square cross-sections. Embodiment where the particulate fluid carrying channel 4a has a triangular cross-section is shown in FIG. 8 and FIG. 9. All the description and meaning of the elements of the drawings related to FIGS. 4 and 5, also apply to FIGS. 8 and 9. The electrodes of the impedance spectrometer are not shown for brevity. It should be stressed that any of the embodiments shown in this disclosure document can be used without any electrodes as impedance spectroscopy is only one of several possible methods that could be used for the analysis of particles (cells). One could also use optical scattering methods or optical fluorescence detection methods similar to the ones in conventional cell cytometers or particle analyzers. Again, there is no wall separating the two channels in FIG. 8, the solid line in FIG. 8 separating the channels is to outline the geometrical boundaries of the channels. FIG. 8 corresponds to the cross-section K-K' of FIG. 9. In this case the particulate containing fluid 4a is guided towards one of the four hydrodynamically favored positions located proximal to the upper left corner of the common channel.

Figure 10:
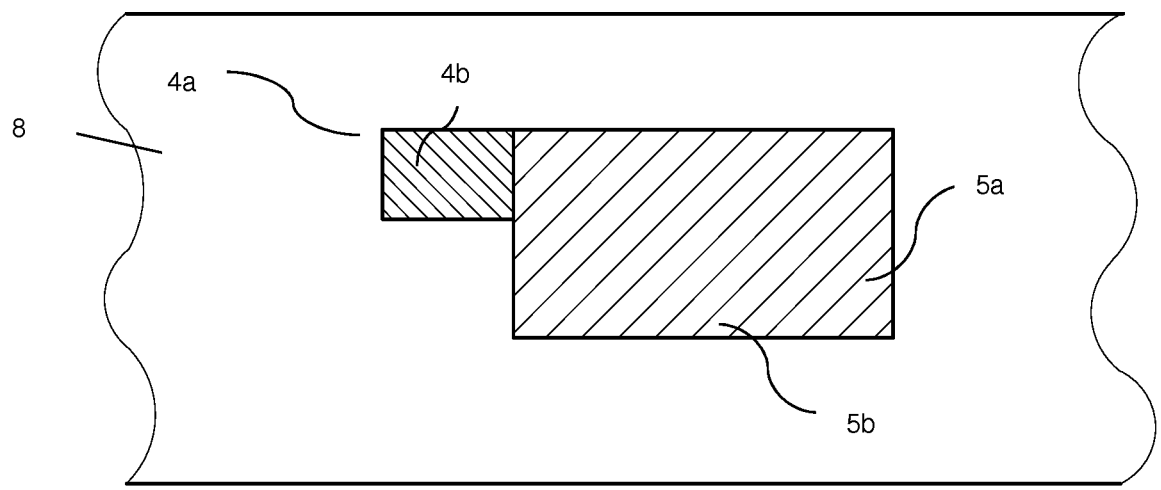
Figure 11:
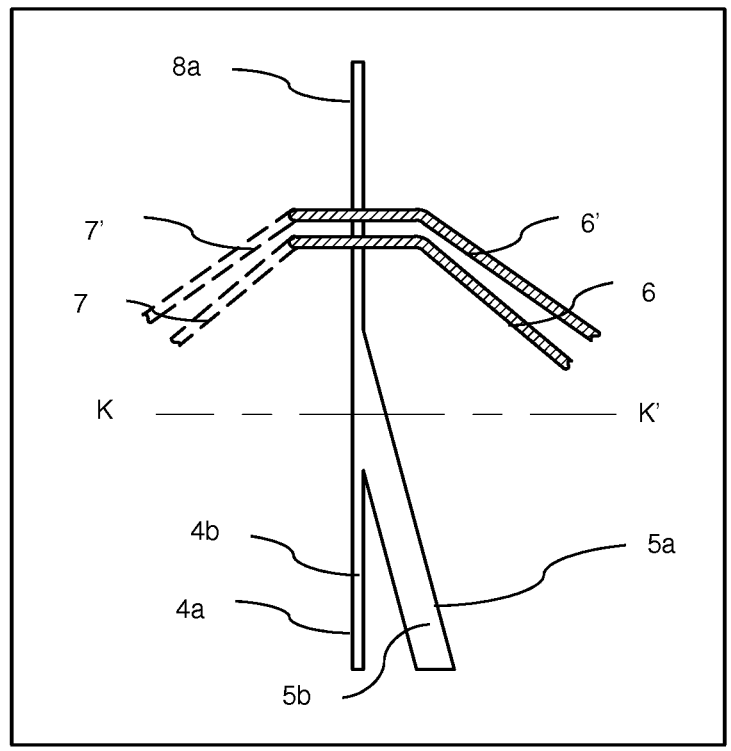

Another embodiment is shown in FIGS. 10 and 11. The description and meaning of the elements of the drawings related to FIGS. 4 and 5 also apply to FIGS. 10 and 11 and will not be repeated for brevity. In this case the particulate containing fluid is guided towards one of the four hydrodynamically favored positions located proximal to the upper left corner of the common channel.

Figure 12:
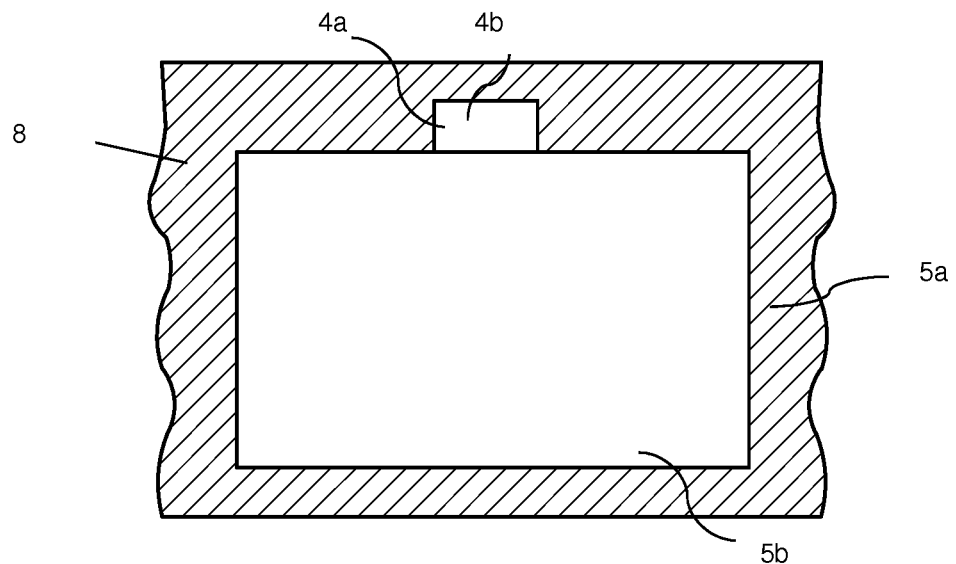
FIG. 12 Cross-section K-K' of embodiment of hydrodynamic focusing microfluidic chip 8 displaying position of merge of particulate containing fluid channel 4a and guidance fluid channel 5a FIG. 13 Top view of embodiment hydrodynamic focusing microfluidic chip 8 with particulate containing channel 4a joining from the top left and guidance fluid channel joining from the bottom.
Figure 13:
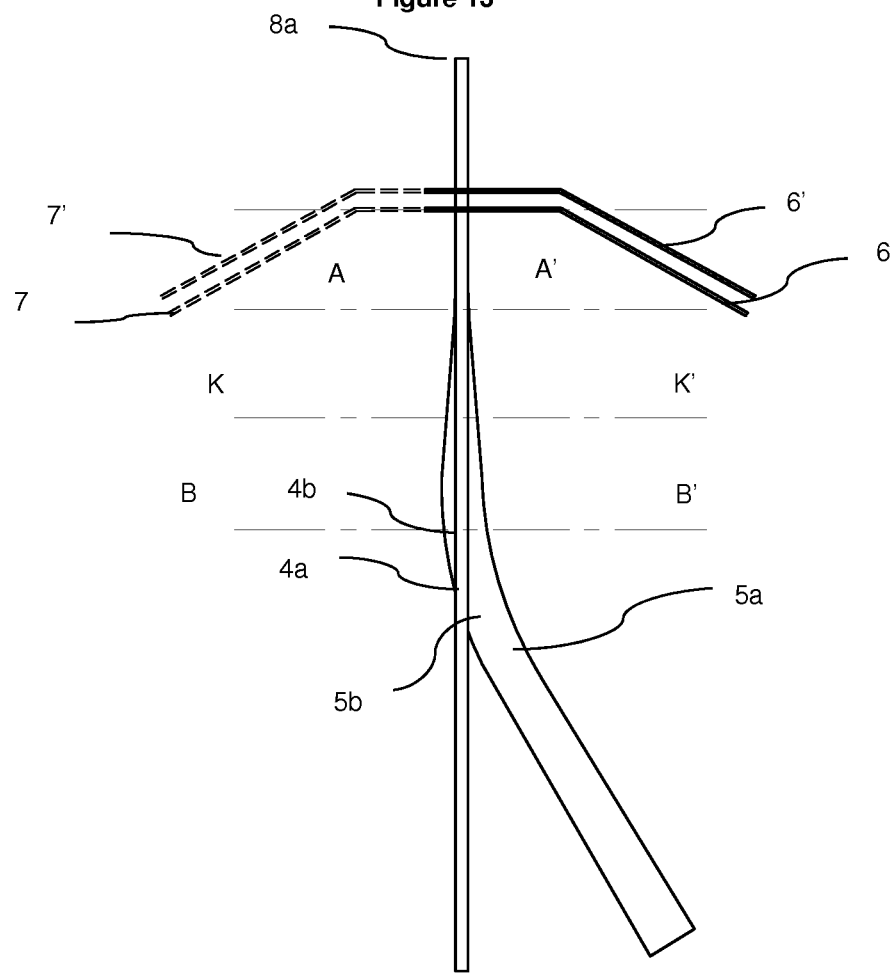

Another embodiment is shown in FIGS. 12 and 13. In the case, particulate fluid containing channel 4a is located above the guidance fluid channel 5a, the same it is in FIGS. 4 and 5. However, unlike the embodiment shown in FIGS. 4 and 5, the two channels are separated by a wall (membrane) 3 in some section of the channel. This section is shown by a dashed triangle in FIG. 13. FIG. 12 corresponds to the cross-section along the line K-K' of FIG. 13. At the area above the line K-K' of FIG. 13, the membrane 3 vanishes and the guidance fluid channel 5a is tapered off to zero width. The guidance fluid channel 5a is tapered off in along the common channel 8a in the range been the points B and A marked on FIG. 13. This is the same as in relation to the previous figures. In this case the particulate containing fluid 4b is guided towards one of the two hydrodynamically favored positions located proximal to the centers of the two opposite sides of the common channel: the upper wall of the common channel, it's ceiling. The other equivalent hydrodynamically favored position located at the floor of the common channel 8a).

Figure 14:
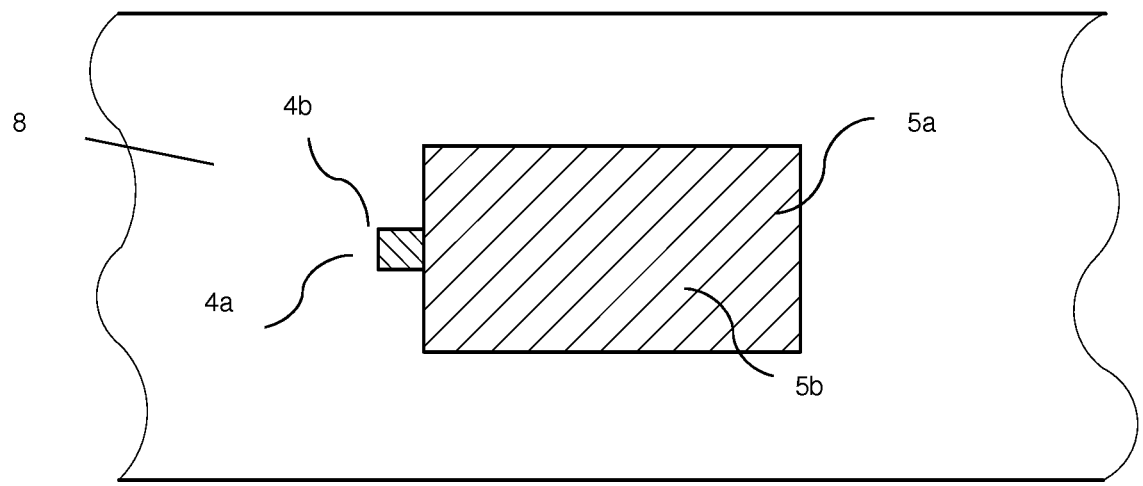
FIG. 14 Cross-section K-K' of embodiment of hydrodynamic focusing microfluidic chip 8 displaying position of merge of particulate containing fluid channel 4a and guidance fluid channel 5a FIG. 15 Top view of embodiment hydrodynamic focusing microfluidic chip 8 with particulate containing channel 4a joining from the center left and guidance fluid channel joining from the right.
Figure 15:
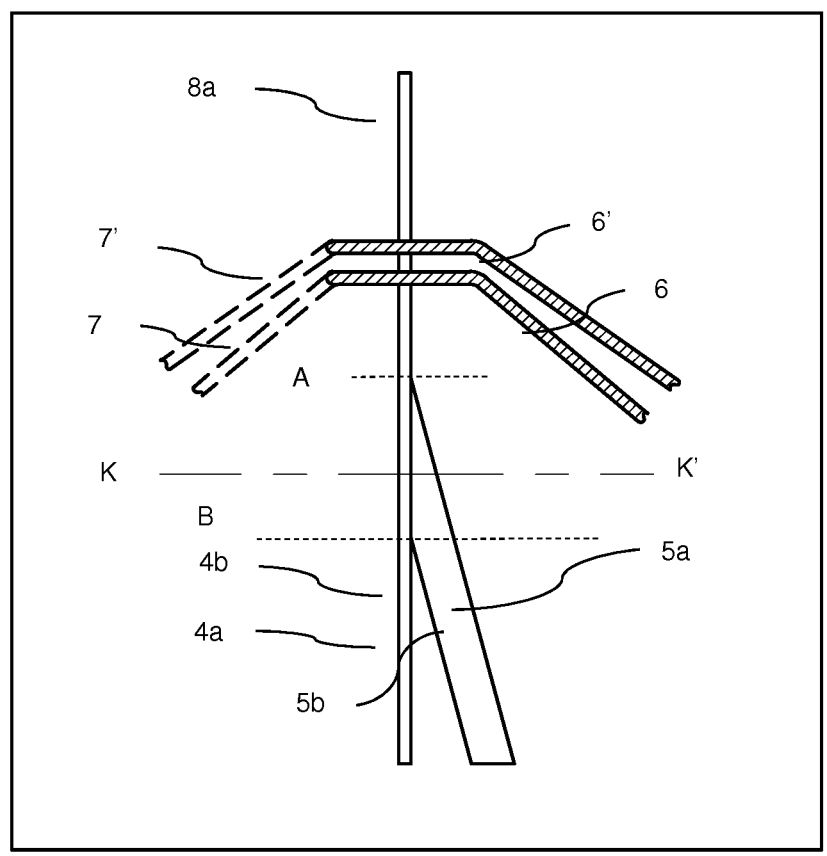

FIGS. 14 and 15 show another embodiment of the apparatus. The notations are the same as in previous figures. The guidance fluid channel 5a is tapered off between the points B and A along the common channel. FIG. 14 represents cross-section along the line K-K' of FIG. 15.

Figure 16:
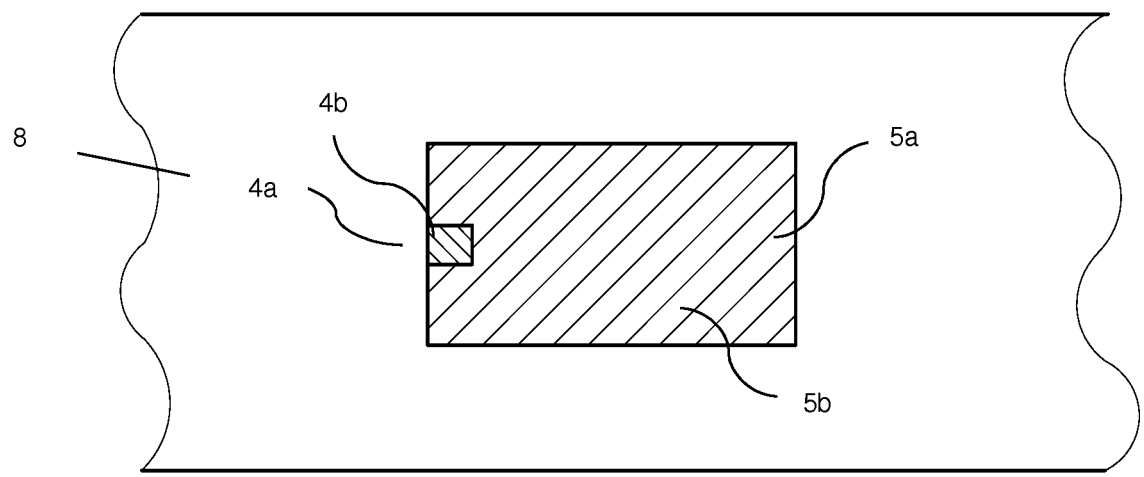
FIG. 16 Cross-section K-K' of embodiment of hydrodynamic focusing microfluidic chip 8 displaying position of merge of particulate containing fluid channel 4a and guidance fluid channel 5a FIG. 17 Top view of embodiment hydrodynamic focusing microfluidic chip 8 with particulate containing channel 4a joining from the center left and guidance fluid channel joining from the top and bottom right.
Figure 17:
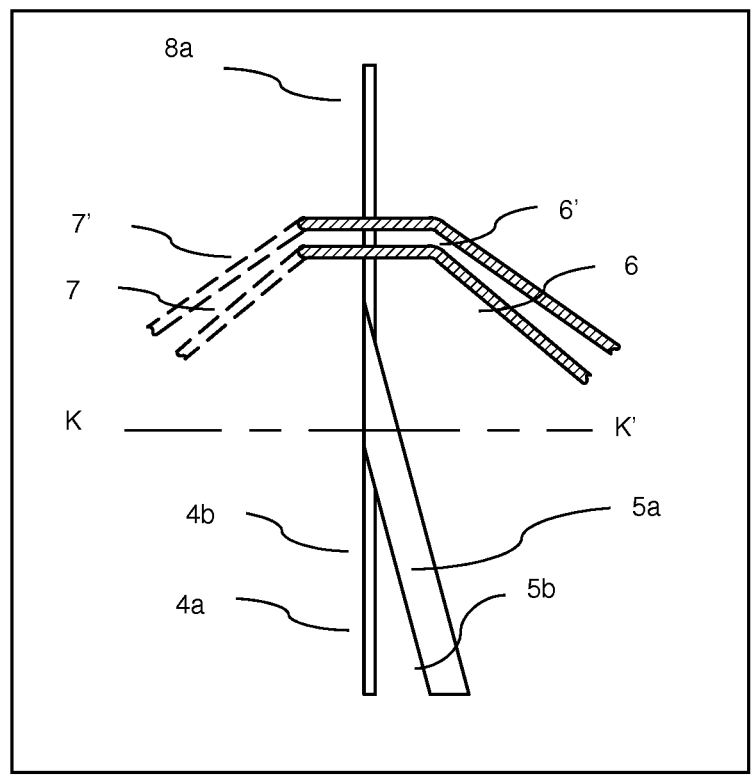

FIGS. 16 and 17 show another embodiment of the apparatus. The notations are the same as in previous figures.

Figure 18A:
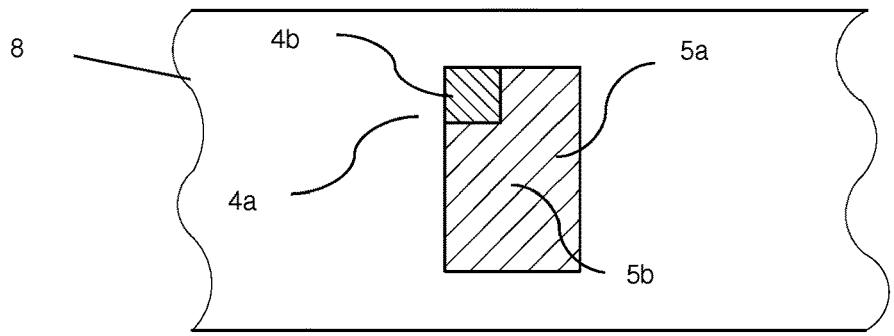
FIG. 18a Cross-section of embodiment of hydrodynamic focusing microfluidic chip 8 displaying position of merge of particulate containing fluid channel 4a and guidance fluid channel 5a FIG. 18b Cross-section of embodiment of hydrodynamic focusing microfluidic chip 8 displaying the common channel 8a and position and orientation of cells 20
Figure 18B:
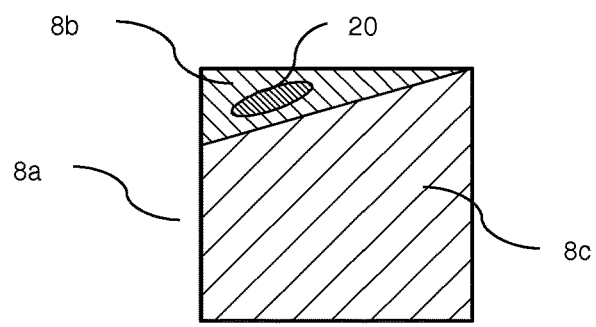
Figure 19A:
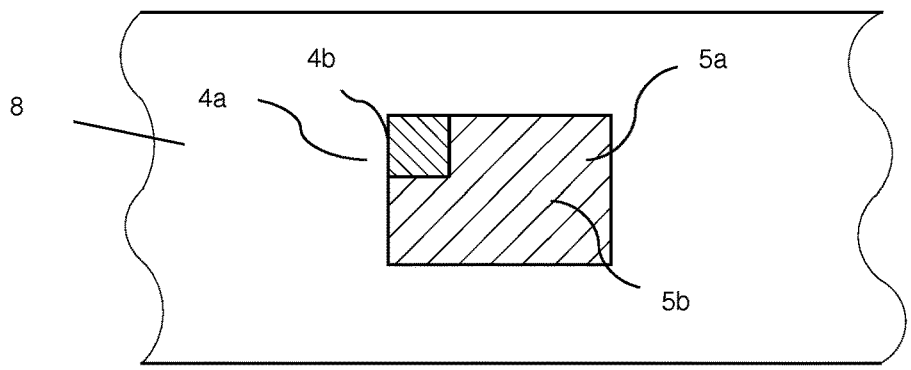
FIG. 19a Cross-section of embodiment of hydrodynamic focusing microfluidic chip 8 displaying position of merge of particulate containing fluid channel 4a and guidance fluid channel 5a FIG. 19b Cross-section of embodiment of hydrodynamic focusing microfluidic chip 8 displaying the common channel 8a and position and orientation of cells 20
Figure 19B:
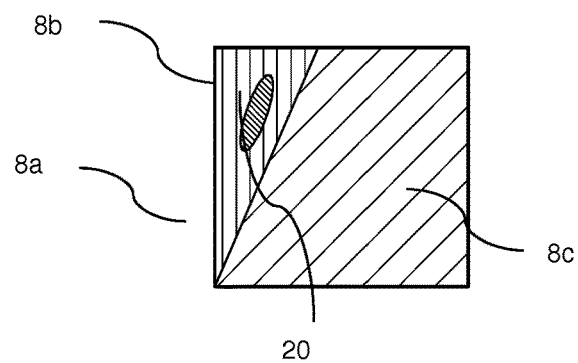

It was explained earlier in the document that in order to improve resolution of the particle (cell) analyzer it is important to align the particles in the same way with respect to the detection system. If the particles/cells are isotropic in their response, then this consideration is irrelevant. However, for anisotropic particles, the consideration is valid. The invention allows achieving better alignment of the particles or cells in addition to confining them into a hydrodynamically favored position. This is explained in FIGS. 18, 19, 20. If the particles are e.g. elongated or discoid in the shape, they will align their long axis parallel to the surface separating the particulate containing fluid from the guidance fluid. FIGS. 18a and 19a show the cross-sections of the particulate containing fluid channel 4a and the guidance fluid channel 5a at the point where they merge. The cross-section areas of each of these channels are the same in FIG. 18a and in FIG. 19a. However, the difference in the aspect ratio of the guidance fluid 5a and particulate containing fluid 4a channels. In the case of embodiment shown in FIG. 18a, the guidance fluid channel 5a is has greater height than the width. In the case of embodiment shown in FIG. 19a, the situation is the inverse. FIGS. 18b and 19b show cross sections of the common channel 8a with the scale five times that of FIGS. 18a and 19a (i.e. common channel is shown enlarged). In the case of embodiment of FIG. 19b the particles or cells 20 are aligned much closer to the vertical line compared to the embodiment of FIG. 18b. This is shown schematically by a shadowed ellipse.

Figure 20A:
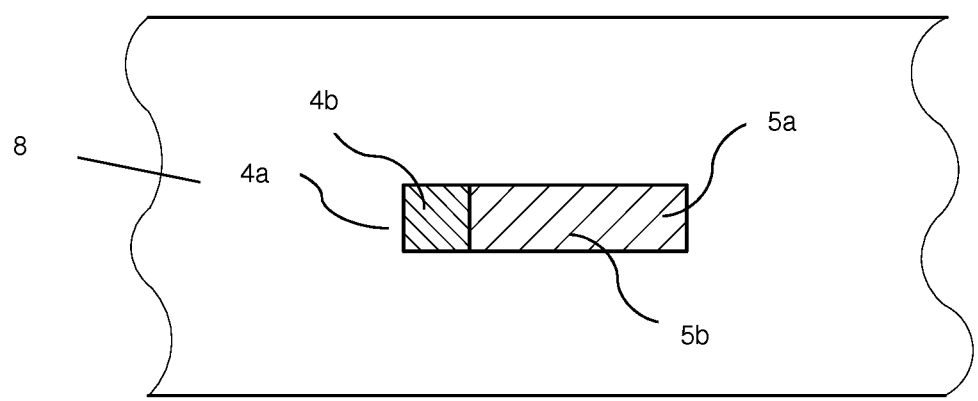
FIG. 20a Cross-section of embodiment of hydrodynamic focusing microfluidic chip 8 displaying position of merge of particulate containing fluid channel 4a and guidance fluid channel 5a FIG. 20b Cross-section of embodiment of hydrodynamic focusing microfluidic chip 8 displaying the common channel 8a and position and orientation of cells 20
Figure 20B:
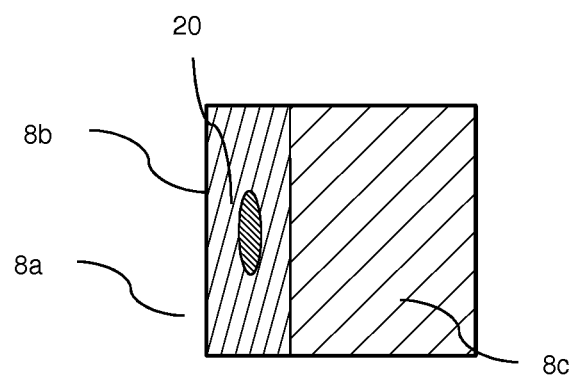

Likewise, in the case of embodiment shown in FIGS. 20a and 20b. In the same way as in FIGS. 18, 19, FIG. 20b shows the cross-section of the common channel 8a short distance away from the cross-section shown in FIG. 20a, some 0.1 mm downstream and the cross-section in FIG. 20b is shown with the scale five times greater than that in FIG. 20a (enlarged). In this case the line separating the particulate containing fluid 4b from the guidance fluid 5b is vertical and the cells or particles 20 will be aligned with the longer axis directed vertically.

Figure 21A:
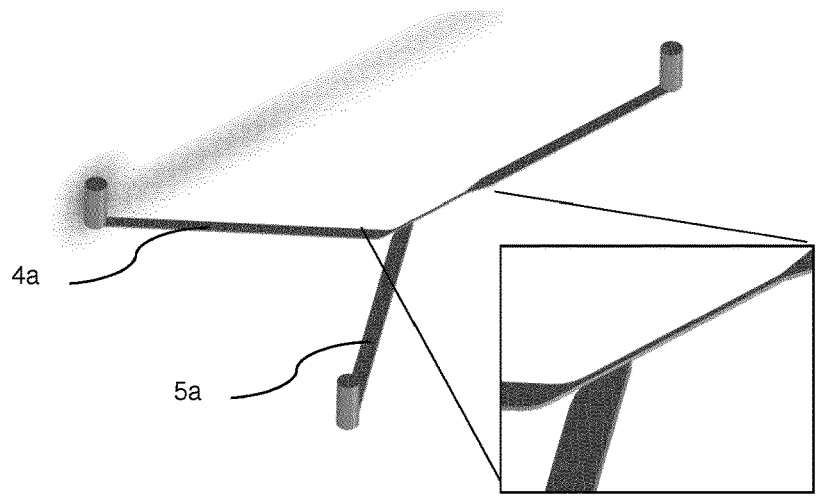
FIG. 21a Isometric view oft of hydrodynamic focusing microfluidic chip for semen cell orientation displaying position of merge of particulate containing fluid/sample fluid channel 4a and guidance fluid channel 5a FIG. 21b Manufactured hydrodynamic focusing microfluidic chip for orientation and impedance detection of semen cells FIG. 21b Microscopic view of hydrodynamic focusing microfluidic chip for orientation and impedance detection of semen cells FIG. 22 Cross-section of embodiment of hydrodynamic focusing microfluidic chip displaying the common channel and position and orientation of semen cells FIG. 23a Impedance diagram of impedance phase versus impedance amplitude for unsorted semen at excitation frequency of 15 MHz and sample flow rate of 30 ul/min and guidance fluid flow stopped FIG. 23b Impedance diagram of impedance phase versus impedance amplitude for unsorted semen at excitation frequency of 15 MHz and sample flow rate of 10 ul/min and guidance fluid flow rate of 20 ul/min FIG. 23c Impedance diagram of impedance phase versus impedance amplitude for unsorted semen at excitation frequency of 15 MHz and sample flow rate of 8 ul/min and guidance fluid flow rate of 22 ul/min FIG. 23d Impedance diagram of impedance phase versus impedance amplitude for unsorted semen at excitation frequency of 15 MHz and sample flow rate of 7 ul/min and guidance fluid flow rate of 23 ul/min FIG. 23e Impedance diagram of impedance phase versus impedance amplitude for unsorted semen at excitation frequency of 15 MHz and sample flow rate of 5 ul/min and guidance fluid flow rate of 25 ul/min FIG. 24a Impedance diagram of impedance phase versus impedance amplitude for unsorted semen at excitation frequency of 15 MHz and sample flow rate of 8 ul/min and guidance fluid flow rate 22 ul/min FIG. 24b Impedance diagram of impedance phase versus impedance amplitude for X sorted semen at excitation frequency of 15 MHz and sample flow rate of 8 ul/min and guidance fluid flow rate 22 ul/min FIG. 24c Impedance diagram of impedance phase versus impedance amplitude for Y sorted semen at excitation frequency of 15 MHz and sample flow rate of 8 ul/min and guidance fluid flow rate 22 ul/min FIG. 25a Impedance diagram of impedance phase versus impedance amplitude for X sorted semen and oriented cells only at excitation frequency of 15 MHz and sample flow rate of 8 ul/min and guidance fluid flow rate 22 ul/min FIG. 25b Impedance diagram of impedance phase versus impedance amplitude for Y sorted semen and oriented cells only at excitation frequency of 15 MHz and sample flow rate of 8 ul/min and guidance fluid flow rate 22 ul/min
Figures 21B, 21C:
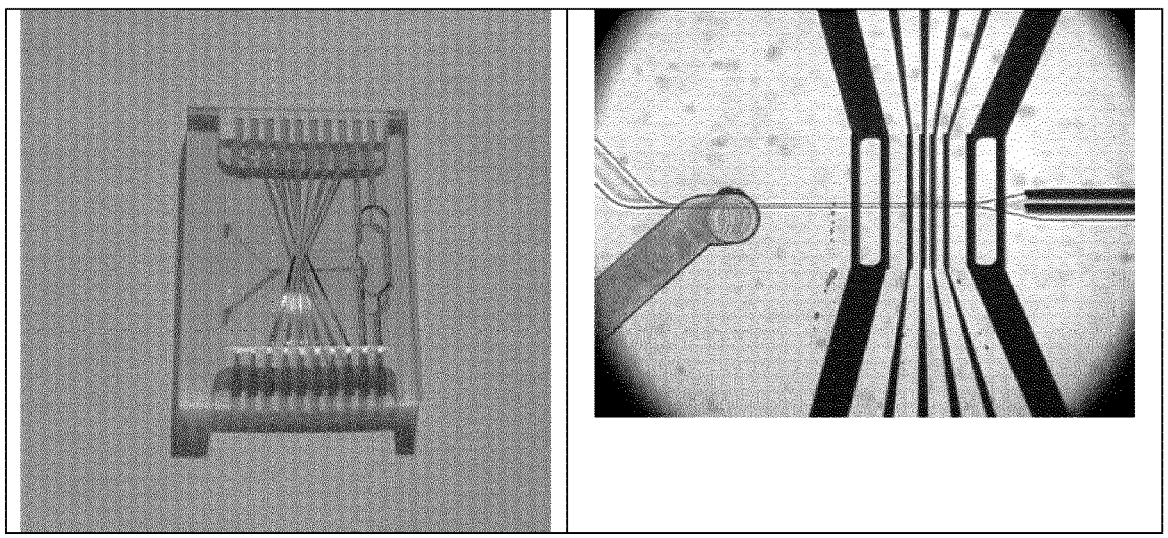

We have used the configuration described above for alignment of bovine semen cells and improvement of the impedance signal to separate X DNA-bearing (female) sperm cells and Y DNA-bearing (male) sperm cells from bulk semen sample. Semen cell are typical example of non-circular cells accurate impedance detection of which are difficult and depends on the orientation and alignment of cells in respect to the surface of the detection electrodes. We have designed the impedance chips with channel configuration displayed in FIG. 21a where semen cells flowing in the sample flow channel 4a coming from the top and left are subjected to the guidance fluid in the guidance fluid channel 5a which is coming from the bottom and from the right. We have then manufactured impedance chips in PMMA plastic material using SU-8 photolithography processing to define microfluidic channels and gold electrode deposition process to define electrode structure (FIG. 21b and FIG. 21c). It is essential that the guidance flow channel has suitable geometry to orient the cells at specific angle. For this investigation, we have selected case 18b dimensions of the guidance channel 200 um×250 um and the sample channel 30 um×30 um.

The chip produced is shown in the FIG. 21b. The close-up of the channel intersection and the detection area is displayed in the FIG. 21c.

To evaluate how well asymmetric focusing chip orients the cell we have carried out several experiments with different 3D focusing ratios:

| Condition/FIG. | Sample flow rate ul/min | Guidance flow rate ul/min |
| --- | --- | --- |
| 1/23a (no focusing) | 30 | 0 |
| 2/23b | 10 | 20 |
| 3/23c | 8 | 22 |
| 4/23d | 7 | 23 |
| 5/23e | 5 | 25 |

Figure 22:
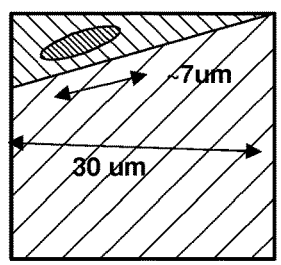
Figure 23A:
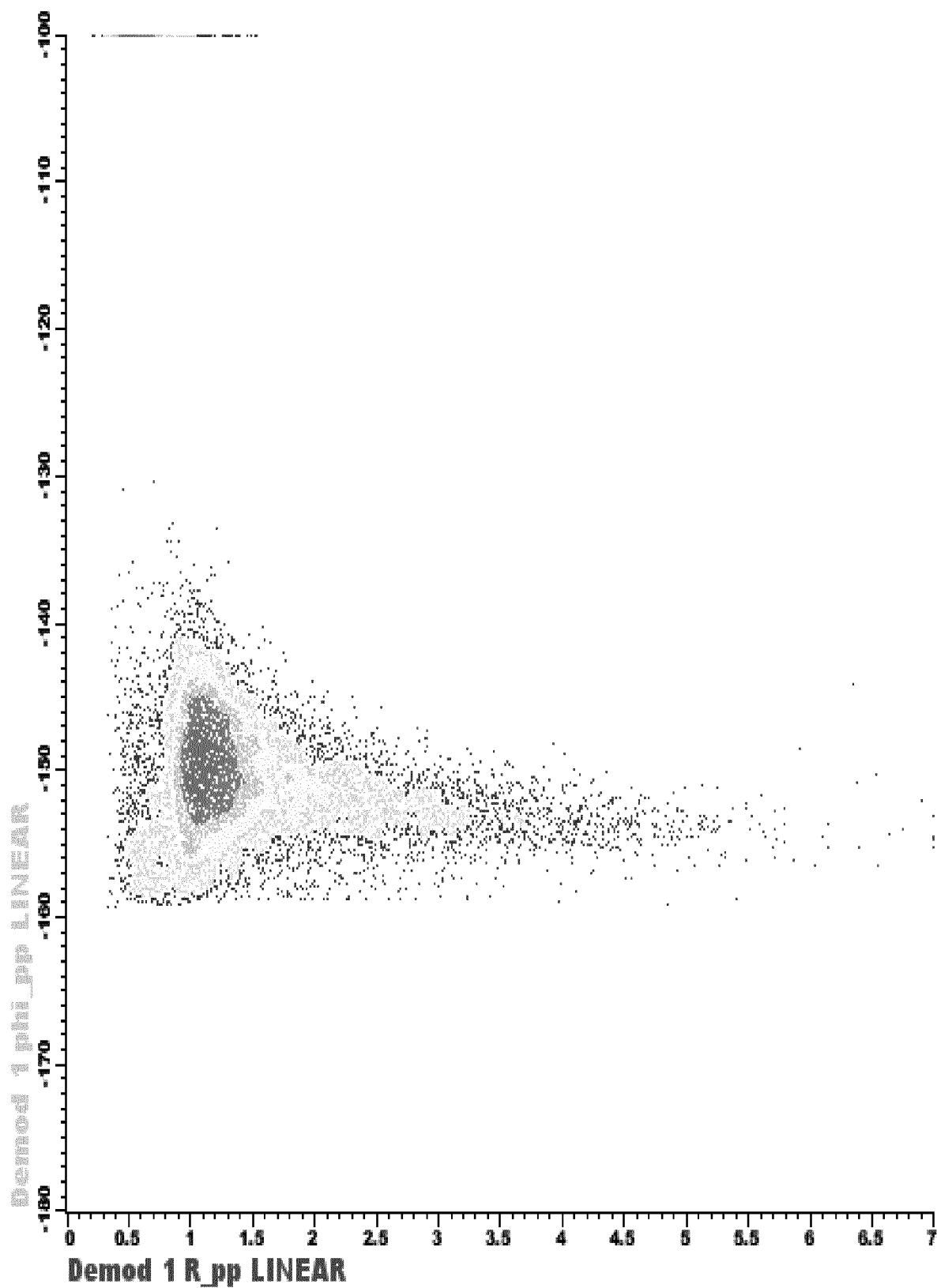
Figure 23B:
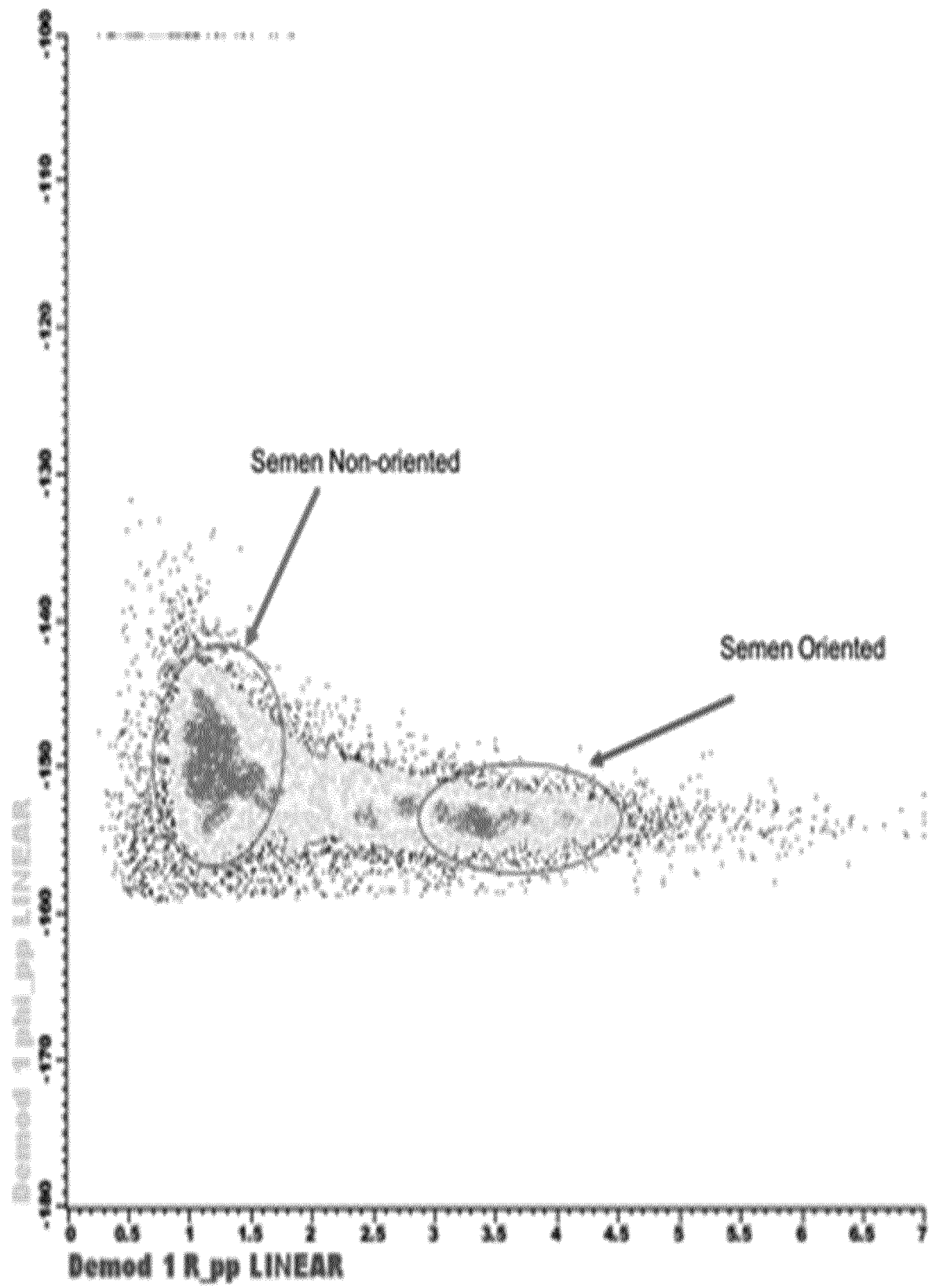
Figure 23C:
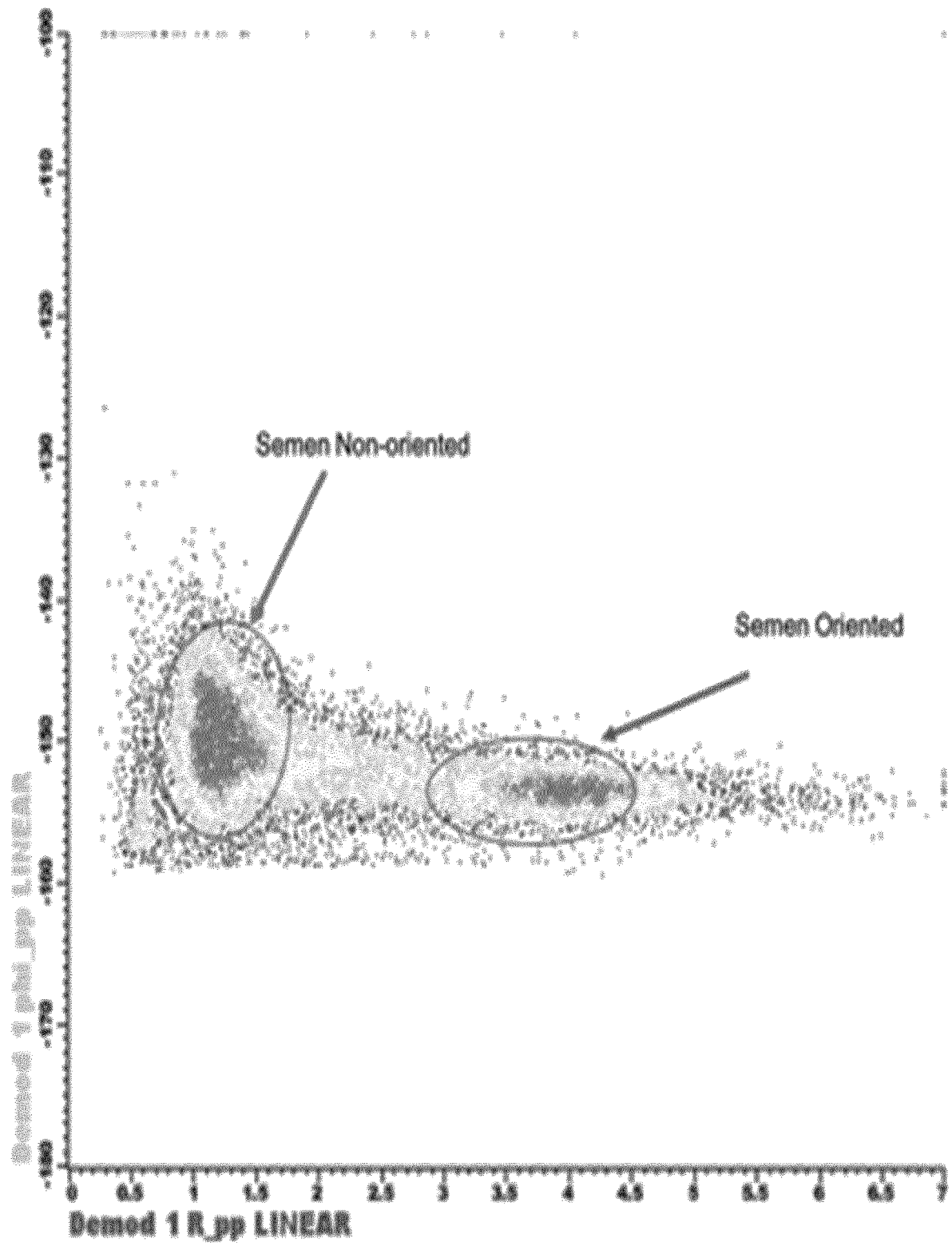
Figure 23D:
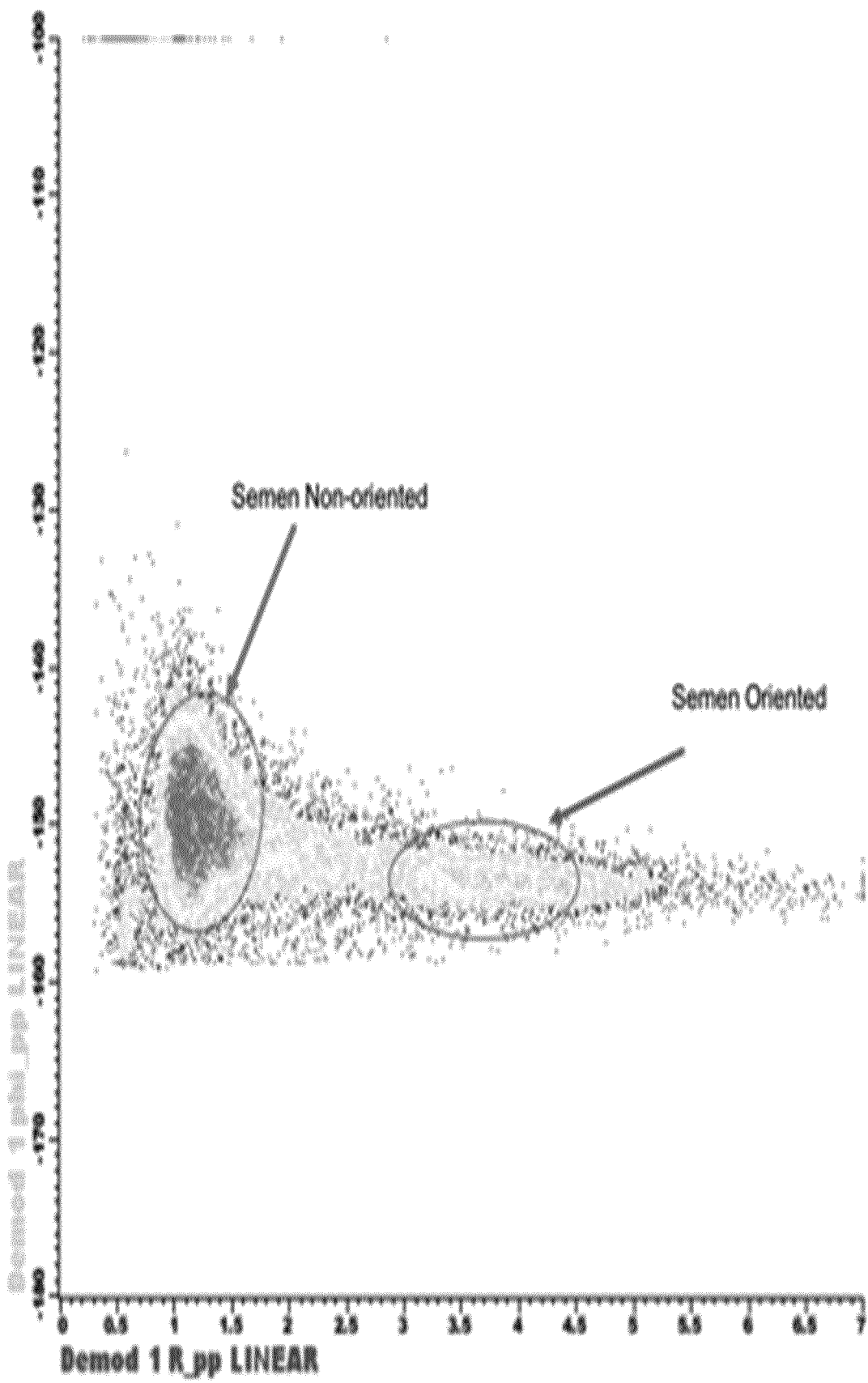
Figure 23E:
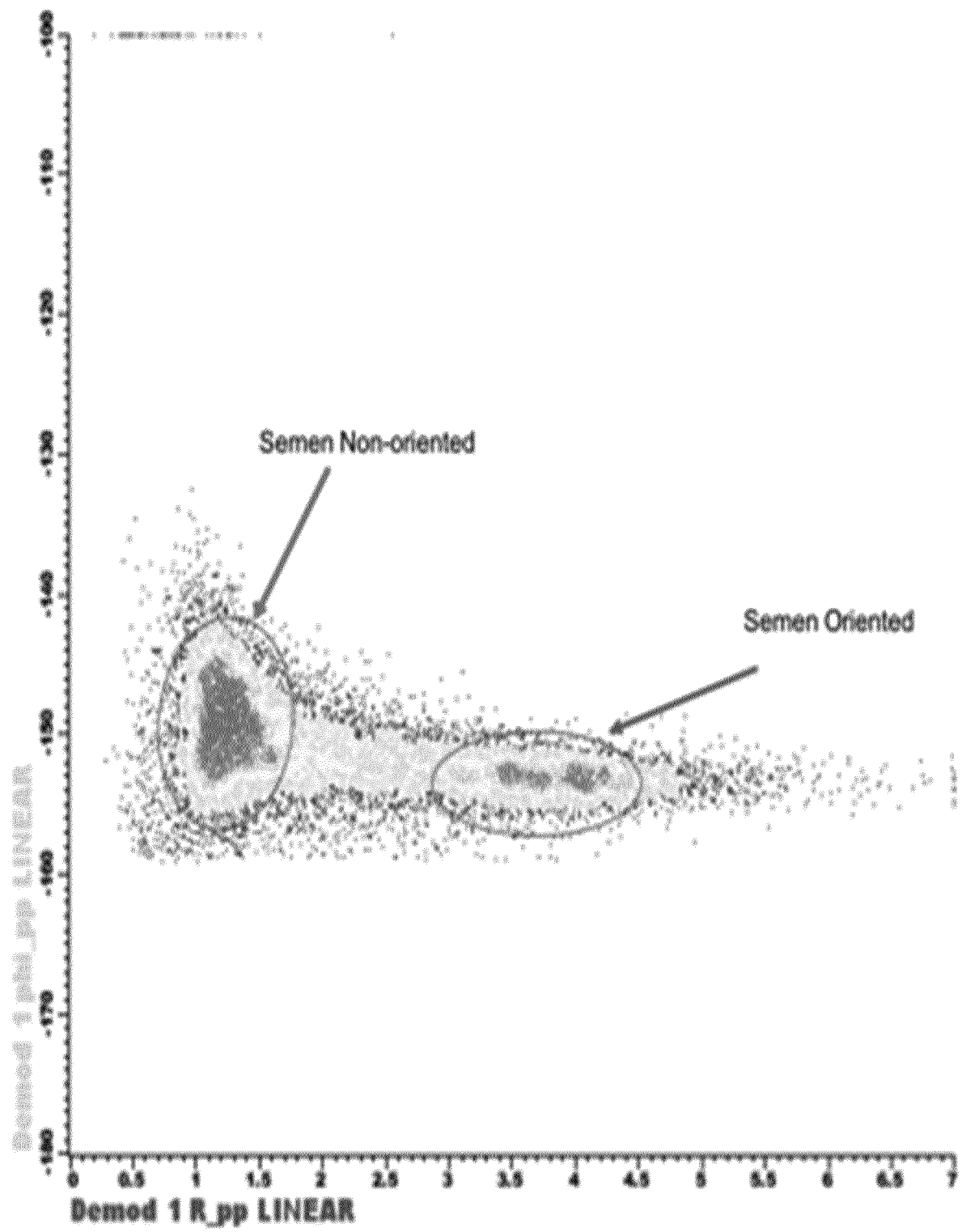

Conditions 3 and 4 were with focusing ratios to match semen size to the dimension of the sample stream according to FIG. 22. The impedance detection has been conducted by triggering on change of the impedance signal at excitation frequency of 0.5 MHz and detecting the change of impedance amplitude and impedance phase at excitation frequency of 15 MHz to differentiate between different subpopulations of cells. The impedance diagrams (X axis-impedance amplitude at 15 MHz and Y axis impedance phase at 15 MHz) are presented in FIGS. 23a-23e. In FIG. 23a we have displayed the result of experiment with no hydrodynamic focusing of cells, where sample flow rate was 30 ul/min and guidance flow was stopped. There is only one population of cells on the impedance diagram and most cells have low impedance signal. This corresponds to the orientation of cells perpendicular to the detection electrodes. As the guidance flow introduced (FIG. 23b) second population appear corresponding to higher impedance amplitude and therefore to orientation parallel to the detection electrode. Two populations are visible: red—non-oriented cells, green—oriented cells. The proportion between non oriented cells to oriented cells—85% to 15%. For condition 3 in FIG. 23c the proportion of orientated cells (red) has increased to 30% versus 70% of non-oriented (green). Also for condition 4 in FIG. 23d the proportion of orientated cells (red) has increased to 35% versus 65% of non-oriented (green). As we continued to increase the guidance fluid flow rate to 25 ul/min the cells had no room to keep desired orientation and therefore rotated out of alignment and proportion has decreased to 95% non-oriented to 5% oriented.

It is evident from FIGS. 23a-23e that the best orientation is achieved when ratio 8 ul/min sample to 22 ul/min guidance and 30 ul/min combined flow rate is used, which directly corresponds to the semen size to microchannel ratio 8/30. As higher squeezing ratio are used it causes semen to lose specific orientation.

Figure 24A:
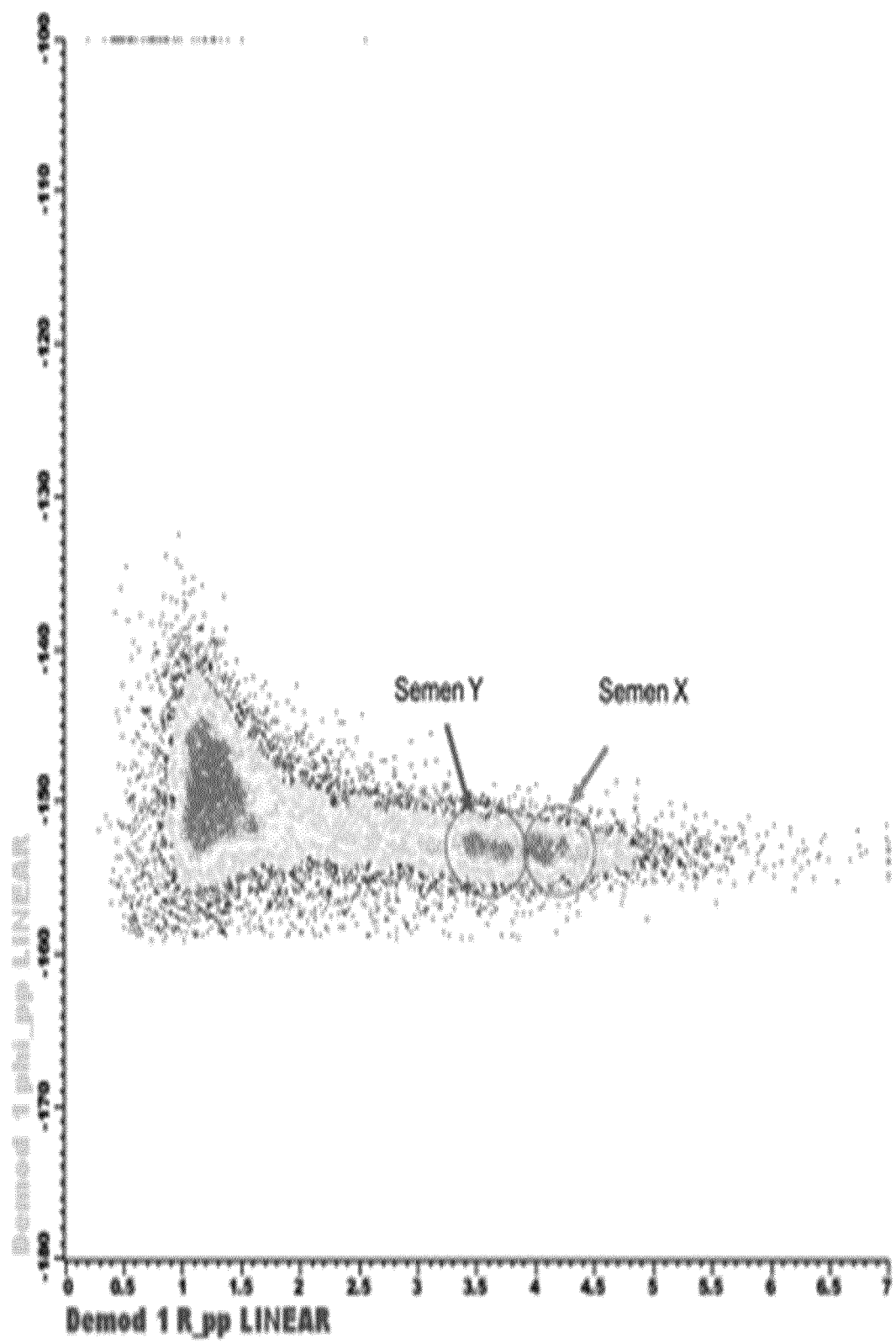
Figure 24B:
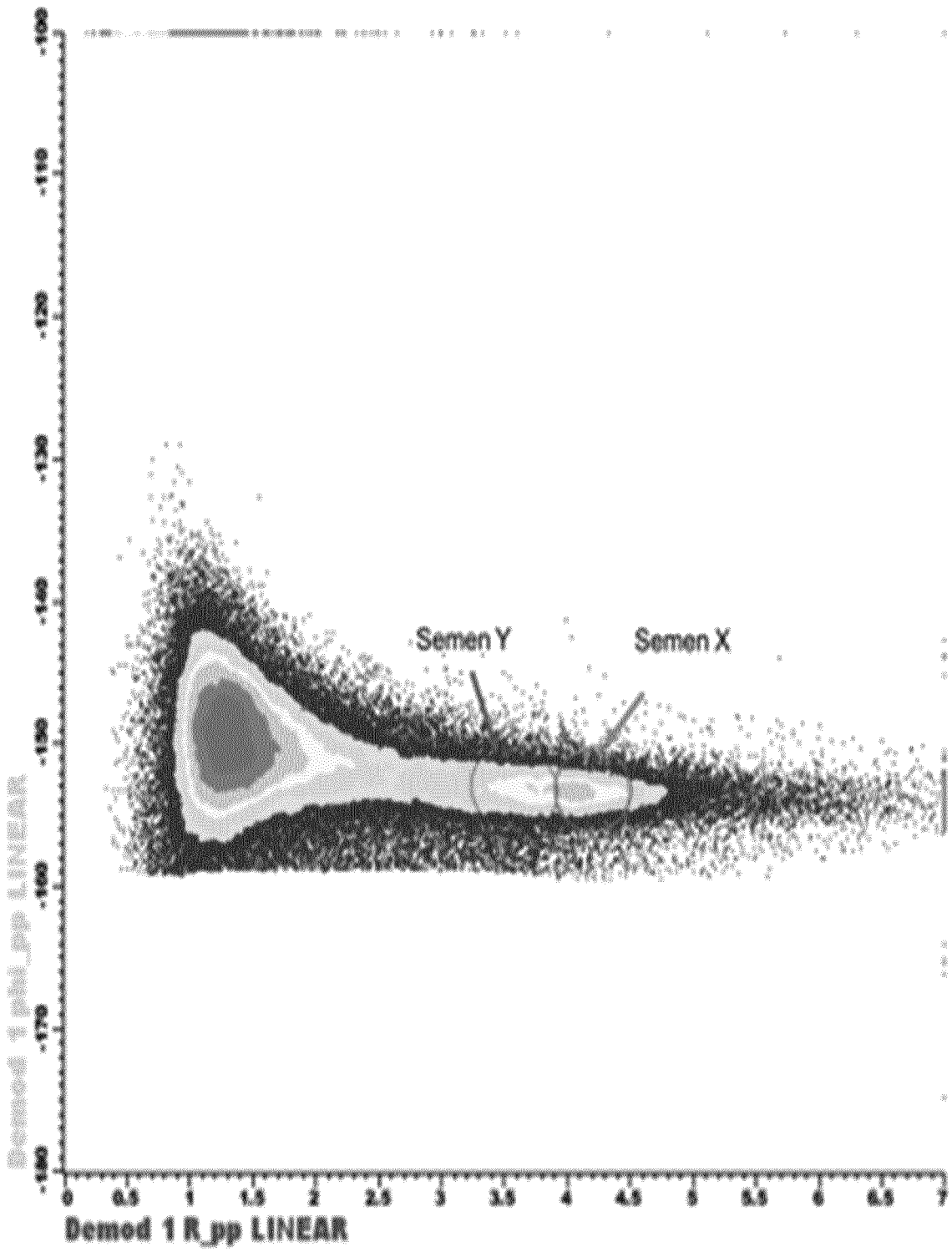
Figure 24C:
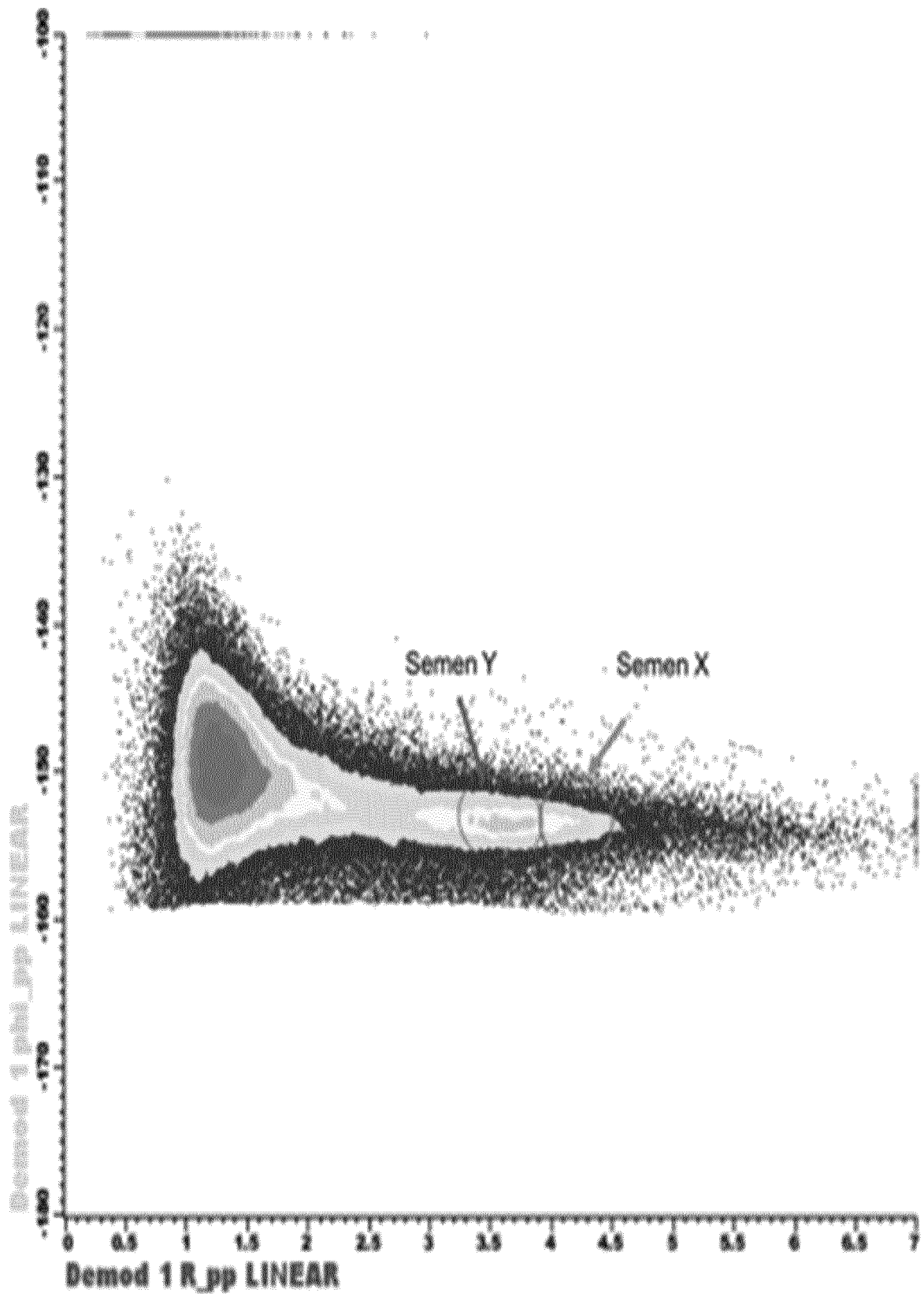
Figure 25A:
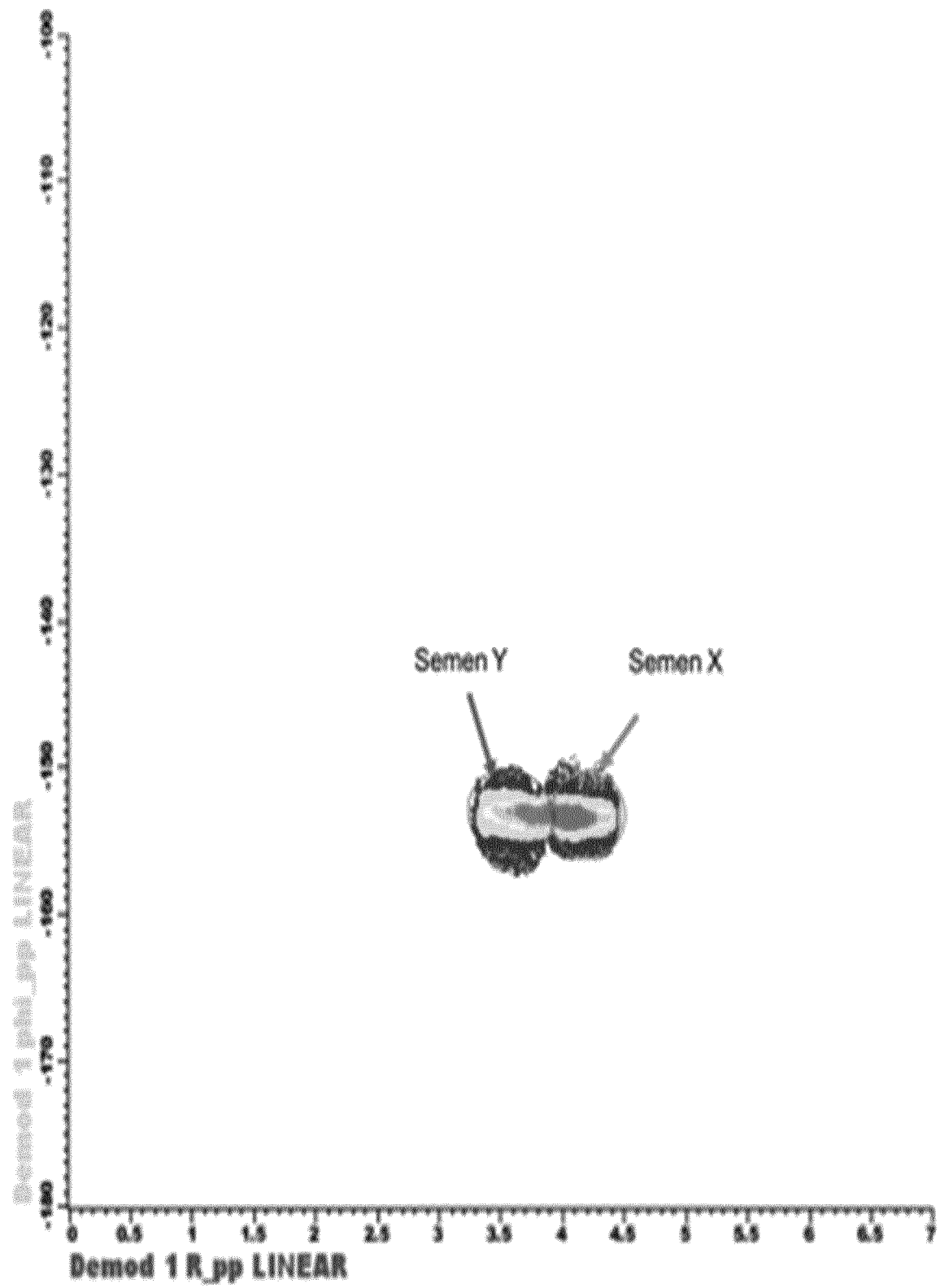
Figure 25B:
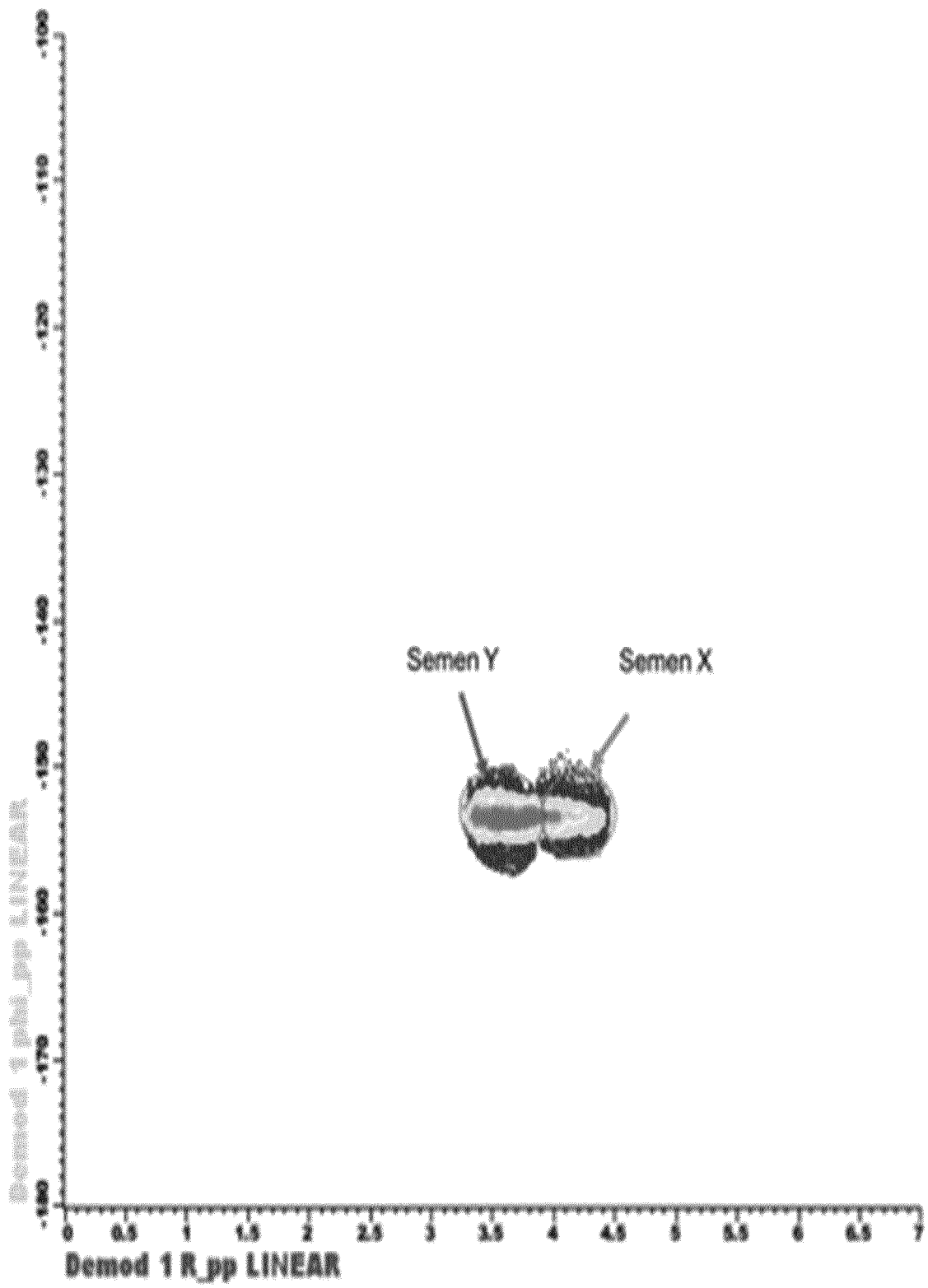

We have further conducted experiments under condition 3 and the corresponding sample flow rate of 8 ul/min and guidance flow rate of 22 ul/min with three different sample: bulk (unsorted semen) containing X and Y bearing cells, pre-sorted X-bearing only semen cells and pre-sorted Y—bearing only semen cells. Results are displayed in FIGS. 24a-24c. It is evident from FIG. 24a when bulk unsorted sample is introduced two distinct populations are visible (X and Y bearing semen cells). When only sorted sample is introduced only one population is visible and median of this population is shifted to the left in case of Y sorted semen 24c and to the right in case of X sorted semen 24b. This is further enhanced when only oriented cells are considered in FIGS. 25a and 25b corresponding to X sorted and Y sorted samples. The results of these experiments highlight important example where the orientation of the cells is crucial for the detection of the minute difference in the impedance of the cells. Without using method of the current invention, we were not able to distinguish any subpopulation in bulk unsorted semen and the impedance signal was low (FIG. 23a). By using current invention, we were able to orient cells in respect to the detection electrode and allow for the detection of individual subpopulations of X and Y bearing semen cells (FIG. 24a-24c).

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

REFERENCES

1. "Fundamentals and Applications of Inertial Microfluidics: A Review", Jun Zhang et. al, Lab on a chip, November 2015
2. "Inertial microfluidic physics", Hamed Amini et. al., Lab on a chip, Issue 15, 2014
3. "Fundamentals of inertial focusing in microchannels", Jian Zhou et.al., Lab on a chip, Issue 6, 2013
4. "Continuous inertial focusing, ordering, and separation of particles in microchannels", Dino Di Carlo et.al, PNAS, volume 104, No 48, November 2007
5. WO 2008/125081 A1, "Method for the hydrodynamic focusing of a fluid and associated assembly" Theisen Janko et al, 23 Oct. 2008
6. "Microflow cytometer with integrated hydrodynamic focusing", Marcin Frankowski et. al., Sensors 2013, 13, 4674-4693
7. "Universally applicable three-dimensional hydrodynamic microfluidic flow focusing", Yu-Jui Chiu et. al., Lab on a chip, 13, 2013
8. US 2009/0283148 A1, "Microchip and channel structure for the same", Masataka Shinoda, May 4 2009.
9. "A robust electrical microcytometer with 3-dimensional hydrofocusing", Nicholas Watkins et.al., Lab on a chip, volume 9, no 22, November 2009
10. "Microfluidic impedance cytometer for platelet analysis", Mikael Evander et.al, Lab on a chip, volume 13, 2013
11. "Multi-wavelength microflow cytometer using groove-generated sheath flow", Joel P. Golden et.al., Lab on a chip, 9, 2009
12. "Two simple and rugged designs for creating microfluidic sheath flow", Peter B. Howell Jr. et. al., Lab on a chip, 8, 2008
13. "A hard microflow cytometer using groove-generated sheath flow for multiplexed bead and cell assays", Abel L. Twangawng et.al., Analytical and Bioanalytical Chemistry, 398:1871-1881, 2010
14. "An Introduction to Fluid Dynamics", Batchelor G. K., Cambridge University Press, pp. 211-215, 1967
15. "Microfluidic Cell Sorting: A Review of the Advances in the Separation of Cells from Debulking to Rare Cell Isolation", C. Wyatt Shields IV et al, Lab Chip. 2015 Feb. 16, 15(5): 1230-1249

The invention claimed is:
1. A microfluidic chip for focusing a stream of particulate containing fluid, the chip comprising:
a sample microfluidic channel configured to receive the stream of particulate containing fluid;
a guidance microfluidic channel configured to receive a stream of guidance fluid;
a common microfluidic channel configured to receive fluid from the sample microfluidic channel and the guidance microfluidic channel, the common microfluidic channel formed by the merging of the sample microfluidic channel and the guidance microfluidic channel at a merging zone, such that the sample microfluidic channel and the guidance microfluidic channel terminate upstream of the merging zone, wherein at least part of the sample microfluidic channel upstream of the merging zone and the common microfluidic channel downstream of the merging zone share a common longitudinal axis; and
a detection zone disposed in the common microfluidic channel having one or more sensors including an excitation electrode and a detection electrode configured to detect AC impedance changes in the common channel that result from the focused stream of particulates passing between the electrodes, and
wherein the merging of the sample microfluidic channel and the guidance microfluidic channel is configured to provide a composite fluid stream containing a focused beam of particulates that is disposed asymmetrically in the common microfluidic channel.
2. A microfluidic chip as claimed in claim 1 in which the sample microfluidic channel merges with the guidance microfluidic channel along only a part of one or two adjacent sides of the guidance microfluidic channel.

3. A microfluidic chip as claimed in claim 1 in which the sample microfluidic channel merges with the guidance microfluidic channel along a corner of the guidance microfluidic channel.

4. A microfluidic chip as claimed in claim 1 in which the sample microfluidic channel has a polygonal cross-sectional area.

5. A microfluidic chip as claimed in claim 1 in which the sample microfluidic channel, guidance microfluidic channel, and common microfluidic channel have a rectangular cross-sectional area.

6. A microfluidic chip as claimed in claim 1 in which the guidance microfluidic channel has a cross sectional area greater than the cross-sectional area of the sample microfluidic channel.

7. A microfluidic chip as claimed in claim 1 in which the guidance microfluidic channel and sample microfluidic channel have different aspect ratios.

8. A microfluidic chip as claimed in claim 1 in which the particulates are aligned along a plane of detection of the one or more sensors or pass the detection zone in single file.

9. A microfluidic chip as claimed in claim 1 in which the one or more sensors are configured to sense at a focal point in the cross-section of the common microfluidic channel that corresponds to the position of the focused beam of particulates.

10. A microfluidic chip as claimed in claim 1 in which the microfluidic channels are configured to provide a composite stream of fluid in which one or both of a sample stream corresponding to the sample microfluidic channel and a guidance stream corresponding to the guidance microfluidic channel has an elongated cross-section.

11. A microfluidic chip as claimed in claim 1 in which the cross-sectional area of the guidance microfluidic channel is at least 2 times greater than the cross-sectional area of the sample microfluidic channel.

12. A microfluidic chip as claimed in claim 1 in which the one or more sensors are disposed at least 100 μm distally downstream from a point at which the sample microfluidic channel and the guidance microfluidic channel are fully merged.

13. A microfluidic chip as claimed in claim 1 in which the one or more sensors are disposed less than 5000 μm distally downstream from a point at which the sample and guidance microfluidic channels are fully merged.

14. A microfluidic chip as claimed in claim 1 in which the merging zone is configured to guide the focused beam of particulates in the common microfluidic channel towards a first hydrodynamic position in the cross section of the common microfluidic channel and away from a second hydrodynamic position in the cross section of the common microfluidic channel, wherein the first hydrodynamic position in the cross section of the common microfluidic channel is closer to the excitation electrode than the second hydrodynamic position.

15. A microfluidic chip for focusing a stream of particulate containing fluid, the chip comprising:
a sample microfluidic channel configured to receive the stream of particulate containing fluid;
a guidance microfluidic channel having a polygonal cross-sectional area and configured to receive a stream of guidance fluid;
a common microfluidic channel having a polygonal cross sectional area formed by the merging at a merging zone of the sample microfluidic channel and the guidance microfluidic channel at an oblique angle of 5° to 60° along part of one side of the guidance microfluidic channel, wherein at least part of the sample microfluidic channel upstream of the merging zone and the common microfluidic channel are co-extensive along a common longitudinal axis, and wherein the guidance microfluidic channel has a longitudinal axis disposed at an angle of 5° to 60° to the common longitudinal axis; and
a detection zone disposed in the common microfluidic channel having one or more sensors including an excitation electrode and a detection electrode configured to detect AC impedance changes in the common microfluidic channel that result from the focused stream of particulates passing between the excitation electrode and the detection electrode,
wherein merging of the sample microfluidic channel and the guidance microfluidic channel is configured to provide a composite fluid stream containing a focused beam of particulates that is disposed asymmetrically in the common microfluidic channel adjacent a corner or side of the common microfluidic channel and wherein the one or more sensors are configured for sensing a characteristic of the focused beam of particulates in the common microfluidic channel,
wherein the microfluidic chip comprises a separation zone disposed in the common microfluidic channel downstream of the detection zone and comprising a force generator configured to exert a force on the focused beam of particulates in the common channel to displace an individual particulate in the stream in response to AC impedance changes detected by the one or more sensors.

16. A microfluidic chip for focusing a stream of particulate containing fluid, the chip comprising:
a sample microfluidic channel configured to receive the stream of particulate containing fluid;
a guidance microfluidic channel configured to receive a stream of guidance fluid;
a common microfluidic channel configured to receive fluid from the sample microfluidic channel and the guidance microfluidic channel, the common microfluidic channel formed by the merging of the sample microfluidic channel and the guidance microfluidic channel at a merging zone, such that the sample microfluidic channel and the guidance microfluidic channel terminate upstream of the merging zone, wherein at least part of the sample microfluidic channel upstream of the merging zone and the common microfluidic channel downstream of the merging zone share a common longitudinal axis; and
a detection zone disposed in the common microfluidic channel having one or more sensors including an excitation electrode and a detection electrode configured to detect DC impedance changes in the common channel that result from the focused stream of particulates passing between the electrodes, and
wherein the merging of the sample microfluidic channel and the guidance microfluidic channel is configured to provide a composite fluid stream containing a focused beam of particulates that is disposed asymmetrically in the common microfluidic channel.

* * * * *